United States Patent [19]

Corbett et al.

[11] 4,387,051
[45] Jun. 7, 1983

[54] β-LACTAM ANTIBIOTICS, THEIR PREPARATION AND THEIR USE IN PHARMACEUTICAL COMPOSITIONS

[75] Inventors: David F. Corbett, Reigate; Robert Southgate, Warnham; Alfred J. Eglington, Brockham, all of England

[73] Assignee: Beecham Group Limited, England

[21] Appl. No.: 201,576

[22] Filed: Oct. 28, 1980

[30] Foreign Application Priority Data

Oct. 29, 1979 [GB] United Kingdom ................ 7937458
Jan. 22, 1980 [GB] United Kingdom ................ 8002105

[51] Int. Cl.³ .......................................... C07D 487/04
[52] U.S. Cl. .............................. 260/245.2 T; 424/114;
424/248.51; 424/246; 424/260; 424/269;
424/270; 424/272; 424/274; 544/61; 544/144;
546/272
[58] Field of Search ................ 260/245.2 T; 546/272;
544/61, 144

[56] References Cited

U.S. PATENT DOCUMENTS

| | | | |
|---|---|---|---|
| 3,926,955 | 12/1975 | Burton et al. | 260/239.1 |
| 4,229,443 | 10/1980 | Binderup | 424/200 |
| 4,231,928 | 11/1980 | Naito et al. | 260/239.1 |
| 4,232,030 | 11/1980 | Christensen et al. | 260/245.2 T |
| 4,237,051 | 12/1980 | McCombie | 260/245.2 R |
| 4,244,965 | 1/1981 | Howarth et al. | 424/272 |
| 4,246,262 | 1/1981 | Vangedal | 424/244 |
| 4,252,722 | 2/1981 | Melilo et al. | 260/245.2 T |
| 4,278,686 | 7/1981 | Corbett et al. | 260/245.2 T |

Primary Examiner—Mary C. Lee
Attorney, Agent, or Firm—Jacobs & Jacobs

[57] ABSTRACT

The present invention provides the compounds of the formula (II):

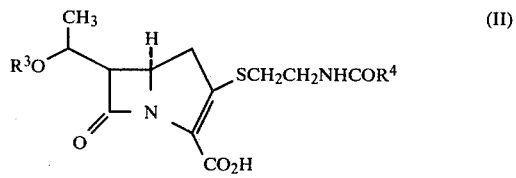

and pharmaceutically acceptable salts and esters thereof wherein $R^3$ is a hydrogen atom, a group $HO_3S-$ or a group $R^5CO$ wherein $R^5$ is $C_{1-6}$ alkyl, $C_{2-6}$ alkenyl, aryl, aryl($C_{1-6}$)alkyl or aryloxy($C_{1-6}$)alkyl; and $R^4$ is an organic group other than methyl bonded to the —CO—NH— moiety via a carbon atom; with the proviso that when $R^3$ is a hydrogen atom or a group $R^5CO$ the stereochemical configuration at the α-carbon atom of the C-6 substituent is S, and with the further proviso that when $R^3$ is a group $HO_3S-$ the hydrogen atoms at C-5 and C-6 are cis. Their use is described as are processes for their preparation. Compounds wherein the $R^4CO-$ moiety is replaced by a hydrogen atom are also prepared.

12 Claims, No Drawings

β-LACTAM ANTIBIOTICS, THEIR PREPARATION AND THEIR USE IN PHARMACEUTICAL COMPOSITIONS

This invention relates to bicyclic carbapenems and in particular to carbapenems possessing an acylaminoethylthio substituent at the C-3 position. These derivatives are useful as antibiotics. This invention also relates to processes for the preparation of such compounds, pharmaceutical compositions comprising such compounds, and methods of treatment comprising the administration of such compounds and compositions.

British Patent Specification No. 1,570,986 discloses inter alia that N-acyl thienamycin derivatives of the formula (I):

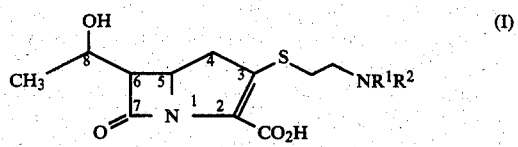

wherein $R^1$ is a hydrogen atom or an acyl group and $R^2$ is an acyl group, are useful antibacterial agents. Thienamycin is known to have the R-configuration at the C-8 position.

It has now been found that carbapenems containing an acetamidoethylthio substituent at C-3 can be converted into novel β-lactam antibiotics which possess desirable antibacterial properties.

Accordingly the present invention provides the compounds of the formula (II):

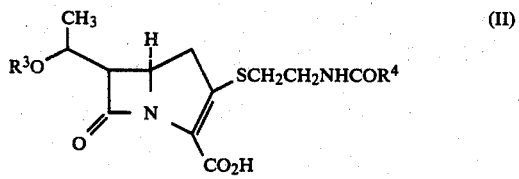

and pharmaceutically acceptable salts and esters thereof wherein $R^3$ is a hydrogen atom, a group $HO_3S-$ or a group $R^5CO$ wherein $R^5$ is $C_{1-6}$ alkyl, $C_{2-6}$ alkenyl, aryl, aryl($C_{1-6}$)alkyl or aryloxy($C_{1-6}$)alkyl; and $R^4$ is an organic group other than methyl bonded to the —CO—NH— moiety via a carbon atom; with the proviso that when $R^3$ is a hydrogen atom or a group $R^5CO$ the stereochemical configuration at the α-carbon atom of the C-6 substituent is S, and with the further proviso that when $R^3$ is a group $HO_3S-$ the hydrogen atoms at C-5 and C-6 are cis.

Suitable groups $R^4CONH$ include those of subformulae (a)–(d):

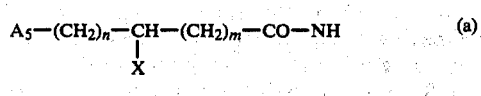

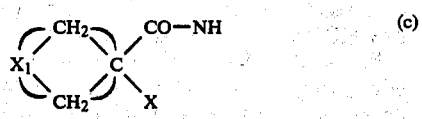

$$A_6-X_2-(CH_2)_n-CO-NH \quad (d)$$

wherein n is 0, 1 or 2; m is 0, 1 or 2; $A_5$ is a hydrogen atom or an alkyl group of 1 to 6 carbon atoms, a cycloalkyl group of 3 to 6 carbon atoms, cyclohexenyl, cyclohexadienyl, phenyl, hydroxyphenyl, thienyl or pyridyl group; X is a hydrogen, fluorine, bromine or chlorine atom, a carboxylic acid, carboxylic ester, azido, tetrazolyl, hydroxy, acyloxy, amino, ureido, guanidino or acylureido group; $A_6$ is an aromatic group such as a phenyl, 2,6-dimethoxyphenyl, 2-alkoxy-1-naphthyl, 3-arylisoxazolyl isothiazolyl, thiazolyl or 3-aryl-5-methylisoxazolyl group; $X_1$ is $CH_2OCH_2$, $CH_2SCH_2$ or $(CH_2)_n$ group; and $X_2$ is an oxygen or sulphur atom. For example, phenylacetamido, p-hydroxyphenylacetamido, o-hydroxyphenylacetamido, m-hydroxyphenylacetamido, α-chlorophenylacetamido, α-bromophenylacetamido, α-carboxyphenylacetamido and esters thereof such as the p-tolyl, indanyl and phenyl esters, α-azidophenylacetamido, α-aminophenylacetamido, α-hydroxyphenylacetamido, α-ureidophenylacetamido, α-guanidinophenylacetamido, α-(acetylureido)phenylacetamido, α-acetoxyphenylacetamido, α-tetrazolylphenylacetamido, acetamido, chloroacetamido, bromoacetamido, propionamido, pyridylacetamido, 2-thienylacetamido, 3-thienylacetamido, 2-thienylpropionamido, 3-thienylpropionamido, α-chloro(p-hydroxyphenyl)acetamido, α-bromo(p-hydroxyphenyl)acetamido, α-carboxy(p-hydroxyphenyl)acetamido and esters thereof such as the p-tolyl, indanyl and phenyl esters, α-amino(p-hydroxyphenyl)acetamido, α-hydroxy(p-hydroxyphenyl)acetamido, α-acetoxy(p-hydroxyphenyl)acetamido, α-ureido(p-hydroxyphenyl)acetamido, α-guanidino(p-hydroxyphenyl)acetamido, α-acetylureido(p-hydroxyphenyl)acetamido, phenoxyacetamido, o-hydroxyphenoxyacetamido, m-hydroxyphenoxyacetamido, p-hydroxyphenoxyacetamido, methoxyacetamido, ethoxyacetamido, α-amino(p-hydroxy)phenoxyacetamido, α-aminophenoxyacetamido, α-acetylphenoxyacetamido, α-acetyl(p-hydroxy)phenylacetamido, α-hydroxyphenoxyacetamido, α-hydroxy(p-hydroxy-phenylacetamido, α-carboxyphenoxyacetamido and esters thereof such as the p-tolyl, indanyl and phenyl esters, α-carboxy(p-hydroxy)phenoxyacetamido and esters thereof such as the p-tolyl, indanyl and phenyl esters, phenoxypropionamido, phenoxybutyramido, benzamido, 2,6-dimethoxybenzamido, 2-ethoxy-1-naphthamido, 2-methoxy-1-naphthamido, 2-propoxy-1-naphthamido, 3-phenyl-5-methyl-4-isoxazolylcarboxamido, 3-o-chlorophenyl-5-methyl-4-isoxazolylcarboxamido, 3-o,o-dichlorophenyl-5-methyl-4-isoxazolylcarboxamido, isothiazolylcarboxamido, 3-o,o-fluorochlorophenyl-5-methyl-4-isoxazolylcarboxamido, 3-phenyl-4-isoxazolylcarboxamido, 3-o-chlorophenyl-4-isoxazolyl-carboxamido, 3-o,o-dichlorophenyl-4-isoxazolylcarboxamido, 3-o,o-fluorochlorophenyl-4-isoxazolylcarboxamido, 1-aminocyclohexyl-1-carboxamido, phenylthioacetamido, phenylthiopropionamido, p-hydroxyphenylthioacetamido, and the like.

More suitably groups $R^4CONH$ include those of the sub-formulae (e) and (f):

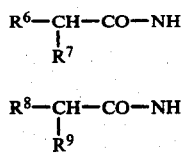

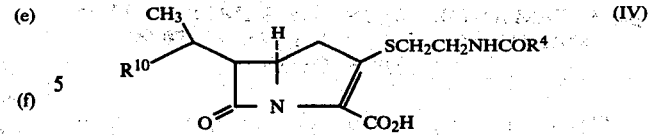

wherein $R^6$ is a phenyl, thienyl or phenoxy group; $R^7$ is a hydrogen atom or methyl group; $R^8$ is a phenyl, p-hydroxyphenyl, thienyl or cyclohexadienyl group; and $R^9$ is a hydroxy, amino or carboxylic acid group or lower alkyl or phenyl, tolyl or indanyl ester thereof.

When used herein the term "lower" means that the group contains 1 to 4 carbon atoms.

A particularly preferred group of the sub-formula (e) is the phenoxyacetamido group. Another particularly preferred group of the sub-formula(e) is the phenylacetamido group.

Further suitable groups of the formula $R^4CONH$ are the amino $C_{1-4}$ alkylamido and $C_{2-4}$ alkylamido groups, for example the propionamido, aminopropionamido and aminoacetamido groups.

Other particularly suitable groups of the formula $R^4$—CO—NH— include the α-methylphenoxyacetamido, α-methylphenylacetamido, α-methyl-2-thienylacetamido, α-methyl-3-thienylacetamido, 2-thienylacetamido, 3-thienylacetamido, α-hydroxyphenylacetamido, α-hydroxy(p-hydroxyphenyl)acetamido, α-hydroxy-2-thienylacetamido, α-hydroxy-3-thienylacetamido, α-aminophenylacetamido, α-amino(p-hydroxyphenyl)acetamido, α-amino-3-thienylacetamido, α-amino-2-thienylacetamido, α-carboxyphenylacetamido, α-carboxy(p-hydroxyphenyl)acetamido, α-carboxy-2-thienylacetamido, α-carboxy-3-thienylacetamido, the methyl, ethyl, propyl, butyl, phenyl, p-tolyl or indanyl ester of α-carboxyphenylacetamido, the methyl, ethyl, propyl, butyl, phenyl, p-tolyl or indanyl ester of α-carboxy(p-hydroxyphenyl)acetamido, the methyl, ethyl, propyl, butyl, phenyl, p-tolyl or indanyl ester of α-carboxy-2-thienylacetamido, and the methyl, ethyl, propyl, butyl, phenyl, p-tolyl or indanyl ester of α-carboxy-3-thienylacetamido.

A preferred sub-group of compounds is that of the formula (III):

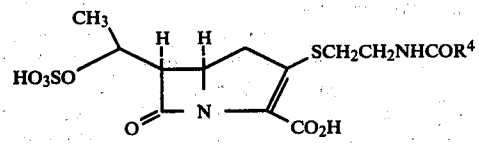

and pharmaceutically acceptable salts and esters thereof wherein $R^4$ is as defined in relation to formula (II).

Suitably the compounds of the formula (III) are in the form of a pharmaceutically acceptable sulphate salt of a pharmaceutically acceptable carboxylate salt, for example the sodium, potassium, magnesium, calcium or ammonium sulphate salt of a sodium, potassium, magnesium, calcium or ammonium carboxylate salt. Favourably the compounds of the formula (III) are in the form of a di-sodium or di-potassium salt, of which the di-sodium is preferred.

A further preferred sub-group of compounds is that of the formula (IV):

and pharmaceutically acceptable salts and esters thereof wherein $R^4$ is as defined in relation to formula (II) and $R^{10}$ is a hydrogen atom or a group $R^5CO$ wherein $R^5$ is as hereinbefore defined in relation to formula (II).

When used herein the term "aryl" with reference to $R^5$ in the compounds of the formula (II) or (IV) means a phenyl group optionally substituted by $C_{1-3}$ alkyl, $C_{1-3}$ alkoxy or chloro or fluoro.

Suitable groups $R^5$ include the methyl, ethyl, n-propyl, n-butyl, phenyl, benzyl and phenoxymethyl groups. Favourably $R^{10}$ is a hydrogen atom or an acetyl group, of which the preferred value of $R^{10}$ is a hydrogen atom.

Suitable pharmaceutically acceptable salts for the compounds of the formula (IV) include the sodium, potassium, magnesium, calcium and ammonium salts; of these the sodium and potassium salts are preferred.

Alternatively the compounds of the formulae (II)—(IV) may be presented as esters at the C-2 position. Suitable esters include those cleavable by chemical methods such as catalytic hydrogenation or hydrolysis, and those which are in-vivo hydrolysable.

Suitably the carboxylic acid is esterified by a group of the sub-formula (g), (h), (i) or (j):

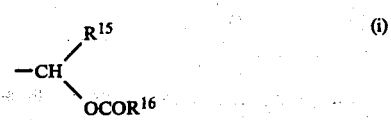

wherein $R^{11}$ is a hydrogen atom or an alkyl, alkenyl or alkynyl group of up to 3 carbon atoms; $R^{12}$ is a hydrogen atom or a methyl group; $R^{13}$ is a phenyl group or a phenyl group substituted by a fluorine, chlorine or bromine atom or a nitro, methyl or methoxy group; $R^{14}$ is a hydrogen atom or a phenyl group or a phenyl group substituted by a fluorine, chlorine or bromine atom or a fluorine, chlorine or bromine atom or a nitro, methyl or methoxy group; $R^{15}$ is a hydrogen atom or a methyl group; $R^{16}$ is a $C_{1-4}$ alkyl, phenyl or $C_{1-4}$ alkoxy group or $R^{15}$ is joined to $R^{16}$ to form a phthalidyl, dimethylphthalidyl or dimethoxyphthalidyl group; and $R^{17}$ is a $C_{1-4}$ alkyl, phenyl, chlorophenyl or nitrophenyl group; or $CHR^{11}R^{12}$ is a phenacyl or bromophenacyl group.

Favourably $R^{11}$ is a hydrogen atom or a methyl, ethyl, vinyl or ethenyl group. Favourably $R^{12}$ is a hydrogen atom. Favourably $R^{13}$ is a phenyl, p-bromophenyl, p-methoxyphenyl or p-nitrophenyl group. Favourably $R^{14}$ is a hydrogen atom. Favourably $R^{16}$ is a methyl, t-butyl or ethoxy group or is joined to $R^{15}$. Favourably $R^{17}$ is a methyl group.

Preferred groups of the sub-formula (g) include the methyl and ethyl groups.

Preferred groups of the sub-formula (h) include the benzyl and p-nitrobenzyl groups.

Preferred groups of the sub-formula (i) include the acetoxymethyl, pivaloyloxymethyl, α-ethoxycarbonyloxymethyl and phthalidyl groups.

A preferred group of the sub-formula (j) is the methoxymethyl group.

Particularly preferred esterifying groups are the p-nitrobenzyl and phthalidyl groups.

Further suitable esters are the tri $C_{1-4}$ alkyl silyl esters, for example the trimethylsilyl ester.

Compounds of the formula (III) may conveniently be presented as a pharmaceutically acceptable salt of the sulphate group and an in-vivo hydrolysable ester of the carboxylic acid group, for example the sulphate may be in the form of a sodium or potassium salt and the carboxylic acid may be esterified as the phthalidyl ester.

Of use as intermediates are di-esters of the compounds of the formula (III), for example the methyl or ethyl sulphate ester of a substituted benzyl carboxylate ester such as the p-nitrobenzyl ester.

It is to be realised that if a free amino group (—NH$_2$) is present in the group $R^4$CONH then a zwitterion of a compound of the formula (II) will be formed. It is also realised that if a carboxylic acid group is present in the $R^4$COHN group then this may optionally be salted by a pharmaceutically acceptable salt such as those hereinbefore defined.

Compounds of this invention wherein $R^3$ is a hydrogen atom or a group $R^5$CO may be provided with cis or trans stereochemistry about the β-lactam ring, that is (5R, 6R) or (5R, 6S). Alternatively they may be provided as mixtures although this is not generally preferred. The compounds of this invention wherein $R^3$ is a HO$_3$S— group are provided with cis stereochemistry about the β-lactam ring, that is (5R, 6R).

The compounds of the formulae (II)–(IV) and their pharmaceutically acceptable salts and in-vivo hydrolysable esters may be employed in the treatment of bacterial infections such as those due to *Staphylococcus aureus, Escherichia coli* and *Klebsiella aerogenes*. Thus the present invention provides a pharmaceutical composition which comprises a compound of the formula (II)–(IV) in the form of its pharmaceutically acceptable salt or in-vivo hydrolysable ester and a pharmaceutically acceptable carrier.

The compositions of this invention may be prepared by conventional methods of preparing antibiotic compositions and in conventional manner may be adapted for oral, topical or parenteral administration.

Aptly, the compositions of this invention are in the form of a unit-dose composition adapted for oral administration.

Alternatively the compositions of this invention are in the form of a unit dose composition adapted for administration by injection.

Unit-dose forms according to this invention will normally contain from 50 to 500 mgs of a compound of this invention, for example about 62.5, 100, 125, 150, 200, 250 or 300 mgs. Such compositions may be administered from 1 to 6 times a day or more conveniently 2, 3 or 4 times a day so that the total daily dose for a 70 kg adult is about 200 to 2000 mg, for example about 400, 600, 750, 1000 or 1500 mg.

The compositions of this invention may be used to treat infections of the respiratory tract, urinary tract or soft tissues in humans, or mastitis in cattle.

The carriers used in the compositions of this invention may include diluents, binders, disintegrants, lubricants, colours, flavouring agents or preservatives in conventional manner. Thus suitable agents include lactose, starch, sucrose, calcium phosphate, sorbitol, polyvinylpyrrolidone, acacia, gelatin, tragacanth, potato starch or polyvinylpolypyrrolidone, magnesium stearate or sodium lauryl sulphate.

Orally administrable forms of the compositions of this invention are most suitably in the form of unit-dose units such as tablets or capsules.

The present invention also provides synergistic pharmaceutical compositions which comprise a pharmaceutical composition as hereinbefore described which also contains a penicillin or a cephalosporin.

Suitable penicillins for inclusion in the compositions of this invention include benzyl penicillin, phenoxymethylpenicillin, ampicillin or a pro-drug therefor, amoxycillin or a pro-drug therefor, carbenicillin or a pro-drug therefor, ticarcillin or a pro-drug therefor, suncillin, sulbenicillin, azlocillin or mezlocillin.

Particularly suitable penicillins for inclusion in orally administrable compositions of this invention include ampicillin and its orally administrable pro-drugs, amoxycillin and its orally administrable pro-drugs and orally administrable pro-drugs of carbenicillin. Thus particularly suitable penicillins include ampicillin anhydrate, ampicillin trihydrate, sodium ampicillin, talampicillin hydrochloride, pivampicillin hydrochloride and bacampicillin hydrochloride; amoxycillin trihydrate, sodium amoxycillin; and the sodium salts of the phenyl and 5-indanyl α-esters of carbenicillin.

A preferred penicillin for inclusion in the orally administrable compositions of this invention is amoxycillin trihydrate. A further preferred penicillin for inclusion in the orally administrable compositions of this invention is ampicillin trihydrate.

Particularly suitable penicillins for inclusion in injectably administrable compositions of this invention include injectable salts such as the sodium salt of ampicillin, amoxycillin, carbenicillin and ticarcillin.

A preferred penicillin for inclusion in the injectably administrable compositions of this invention is sodium amoxycillin. A further preferred penicillin for inclusion in the injectably administrable compositions of this invention is sodium ampicillin.

Particularly suitable cephalosporins for inclusion in the compositions of this invention include cephaloridine, cephalexin, cephradine, cefazolin and cephalothin.

A particularly suitable cephalosporin for inclusion in the orally administrable compositions of this invention is cephalexin.

Particularly suitable cephalosporins for inclusions in the injectably administrable compositions of this invention include cephaloridine, cefazolin and cephradine, generally as their pharmaceutically acceptable salt.

The weight ratio between compound of this invention and penicillin or cephalosporin is generally from 10:1 to 1:10, more usually from 5:1 to 1:5 and normally from 3:1 to 1:3.

The pencillin or cephalosporin is generally utilised in its conventionally administered amount.

In another aspect of this invention there is provided a process for the preparation of a compound of the formula (V):

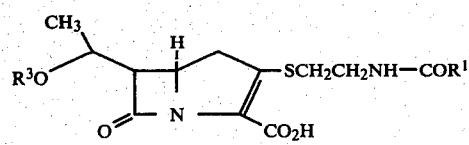 (V)

or pharmaceutically acceptable salt or ester thereof wherein $R^3$ is as hereinbefore defined and $R^{18}$ is an organic group bonded to the —CO—NH— moiety via a carbon atom, which process comprises the reaction of an ester of a compound of the formula (VI):

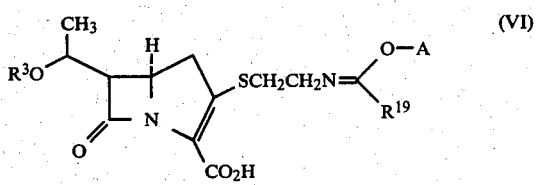 (VI)

wherein $R^3$ is as defined in relation to formula (II) except that any group capable of being acylated is optionally protected, A is a $C_{1-8}$ hydrocarbon group, and $R^{19}$ is a group of the sub-formula (a)–(d) as hereinbefore defined wherein the moiety —CO—NH is not present; with a catalyst in the presence of an acid acceptor with an N-acylating derivative of a carboxylic acid of the formula (VII):

$R^{18}$—$CO_2H$  (VII)

wherein any group capable of being acylated is optionally protected, and thereafter if necessary:
(i) converting any cleavable ester group into a free acid, a pharmaceutically acceptable salt or different ester,
(ii) removing any protecting groups.

The compound of the formula (VI) may be presented with either R or S sterochemical configuration at the C-8 position.

Suitably the catalyst is a transition metal catalyst for example a platinium, rhodium or palladium catalyst, of these palladium is preferred especially in the form of palladium chloride.

Suitably A is a $C_{1-8}$ hydrocarbon group, more suitably A is $C_{1-6}$ hydrocarbon group such as a methyl, ethyl, isopropyl, n-propyl, n-butyl, isobutyl, tert-butyl, n-pentyl, iso-aryl, n-hexyl, cyclopentyl or cyclohexyl group. Most suitably A is a methyl, ethyl, n-propyl or n-butyl group. A preferred value of A is a methyl group.

The acid acceptor used in the process is suitably a base, more suitably an organic base such as an organic amine, for example tertiary amines such as triethylamine, trimethylamine or N-($C_{1-4}$)alkylmorpholine, and pyridine or dimethylaminopyridine. A preferred base is N-methylmorpholine. Another preferred base is pyridine. A further preferred base is 4-dimethylaminopyridine.

The term "acylating derivative of a carboxylic acid" includes any N-acylating compound suitable for the performance of analogous reactions with 6-aminopenicillanic acid or 7-aminocephalosporanic acid or salts or esters thereof for example an acid halide, a mixed anhydride or other reactive derivative such as that produced by the reaction of an acid with an enzyme or a condensation promoting agent such as dicyclohexylcarbodi-imide or its chemical equivalent. Reactive groups present in such acylating agents may be protected in conventional manner.

Such N-acylating compounds may be summarised by the formula (VIII):

$R^{18}$—CO—W  (VIII)

wherein $R^{18}$ is as defined in relation to a compound of formula (V) and W is a readily displaceable group.

Most suitably W is a bromine atom.
Preferably W is a chlorine atom.
Suitable protecting groups for the group $R^3$ include those removable by hydrogenolysis or hydrolysis, for example p-nitrobenzyloxycarbonyl or tri $C_{1-4}$ alkyl silyl such as trimethylsilyl and tert-butyldimethylsilyl are suitable protecting groups for a hydroxy function.

When the group $R^3$ is $HO_3S$— suitably for use as an intermediate, for example in the compound of the formula (V), the sulphate moiety is provided in the form of a substituted ammonium salt, for example a tetra-($C_{1-6}$ alkyl)substituted ammonium salt such as the tetra-n-butylammonium salt.

The above process is suitably performed in two stages with the palladium complex being isolated prior to treatment with the acylating agent and base. The first stage of the process is suitably carried out in a solvent such as aqueous tetrahydrofuran or aqueous dioxan. This solvent mixture is suitably maintained at a pH of from 6 to 8 preferably at about pH 7, by the use of a conventional buffer solution. This stage of the process is performed at a non-extreme temperature for example from 5° C.-30° C., preferably from 12° C.-25° C. and most conveniently at ambient temperature.

The palladium complex formed by the first stage of the process is isolated and then treated with the N-acylating agent in the presence of an acid acceptor. This second stage of the process is performed in an organic solvent such as dichloromethane, chloroform or dichloroethane, at a suitable non-extreme temperature for example from 0° C.-30° C., preferably from 12° C.-25° C. and most conveniently at ambient temperature.

Suitable methods of converting a cleavable ester into a free acid or pharmaceutically acceptable salt include hydrogenation for example in the presence of a transition metal catalyst. The catalyst we have preferred to use is palladium for example in the form of 5% or 10% palladium on carbon. A low, medium or high pressure of hydrogen may be employed in this reaction, for example from 1 to 6 atmospheres. However, it is normal to use an atmospheric pressure of hydrogen.

The reaction is normally carried out at a non-extreme temperature, for example from 0° C. to 30° C. and more usually from 12° C. to 25° C. It is generally convenient to carry out the reaction at ambient temperature. Suitably solvents for carrying out the hydrogenation include dioxan, tetrahydrofuran, or mixtures of such solvents in the presence of water. Favoured solvents are aqueous tetrahydrofuran. A favoured hydrogenolysable ester is the p-nitrobenzyl ester. The hydrogenation reaction may be performed in the presence of a base in which case a salt of a compound of the formula (V) is obtained directly. Alternatively a carboxylic acid of the formula (V) is salified in conventional manner for example by using a carbonate or bicarbonate such as sodium bicarbonate or potassium bicarbonate to form a salt of a compound of the formula (V).

Re-esterification of the carboxyl group of a salt of a compound of the formula (V) may be effected in conventional manner. Suitable methods include the reaction of an alkali metal salt of the compound of the formula (V) such as the sodium or potassium salt with a reactive halide or sulphonate ester such as a bromide, chloride, mesylate or tosylate. Such esterifications may be carried out under conventional conditions for example in dimethylformamide at room temperature.

A carboxylate ester of a sodium or potassium sulphate salt of a compound of the formula (V) may be prepared by the reaction of a tetra-substituted ammonium sulphate salt of a carboxylate ester of a compound of the formula (V) with a sodium or potassium halide for example sodium iodide or potassium iodide. Such a reaction is performed in an organic solvent such as acetone.

In a particularly preferred aspect of this invention the group $R^3$ in a compound of the formula (VI) is a trimethylsilyl group and the carboxylate ester is a trimethylsilyl ester so that on work-up of the acylation reaction both trimethylsilyl protecting groups are readily hydrolysed to afford a compound of the formula (V) or salt thereof wherein $R^3$ is a hydrogen atom.

In a further aspect of this invention an alternative process is provided for the preparation of an ester of a compound of the formula (V) which process comprises the hydrolysis of an ester of a compound of the formula (VI) as hereinbefore defined, and subsequently treating the free amino compound so formed with a reactive acylating derivative of a carboxylic acid of the formula (VII) as hereinbefore defined.

Suitably the hydrolysis is performed under neutral or acidic conditions, for example using a hydrated acidic catalyst. It is preferred that not more than one equivalent of an acid catalyst is used.

Suitable acid catalysts are those that do not cause substantial degradation of the compounds of the formula (V) and (VI), for example p-toluenesulphonic acid and tetra-n-butylammonium hydrogen sulphate.

A preferred acidic catalyst is p-toluenesulphonic acid.

The first stage of this process is performed in an organic solvent such as dichloromethane, chloroform, ethyl acetate, ether, dioxan, tetrahydrofuran or in a mixture of such solvents. This stage of the reaction is performed at a non-extreme temperature for example from 0° C.-30° C., preferably from 12° C.-25° C. and most conveniently at ambient temperature.

The second stage of this process is performed as for the acylation of the palladium complex described hereinabove.

In a further aspect of this invention a process is provided for the preparation of an ester of a compound of the formula (VI) which process comprises the reaction of a carboxylate ester of a compound of the formula (IX):

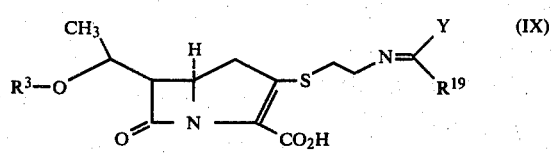

wherein $R^3$ and $R^{19}$ are as defined in relation to a compound of the formula (VI), and Y is a chlorine or bromine atom; with an alcohol AOH in the presence of a base, wherein A is as defined in relation to a compound of formula (VI).

Suitably the base is an organic amine, for example, a tertiary amine such as triethylamine, trimethylamine or N-alkylmorpholine, and pyridine. A preferred base is N-methylmorpholine.

Suitably Y is a chlorine atom. Suitably Y is a bromine atom.

The amount of alcohol AOH is suitably more than one mole equivalent. We have found it convenient to use a large excess of alcohol AOH.

Suitably the reaction of an ester of a compound of the formula (IX) with an alcohol AOH is carried out at a temperature between $-30°$ C. and $+25°$ C.

Most suitably the temperature is between $-10°$ C. and $+20°$ C. A preferred temperature is at about 10° C.

In another aspect of this invention a process is provided for the preparation of an ester of a compound of the formula (IX) which process comprises the reaction of an ester of a compound of the formula (X):

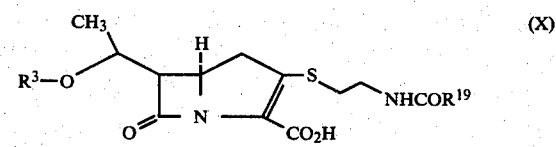

wherein $R^3$ and $R^{19}$ are as defined in relation to a compound of the formula (VI), with an imino-halogenating agent and a base.

Suitably 1 to 10 mole equivalents of the base are used, more suitably 1 to 5 mole equivalents and preferably 2 to 3 mole equivalents of the base are used.

The imino-halogenating agent used is one which will convert an amide group —NH—CO— to an iminohalide group —N=CY— wherein Y is as defined in relation to a compound of the formula (IX), for example, phosphorus pentachloride, phosphorus pentabromide, thionyl chloride, thionyl bromide, phosgene, phosphorus trichloride, phosphorus tribromide, phosphorus oxychloride, phosphorus oxybromide and the like.

The solvent used is suitably an inert organic solvent such as dichloromethane, chloroform, carbon tetrachloride, dichloroethane, tetrahydrofuran, dioxan or the like.

The reaction is performed in the presence of a base. Suitably the base is an organic base for example a tertiary amine such as triethylamine, trimethylamine or N-alkylmorpholine, and pyridine. Most suitably the organic base is N-methylmorpholine.

We have also found it most convenient to use triphenylphosphine or tri-p-methoxyphenylphosphine with carbon tetrahalide as a iminohalogenating agent for example triphenylphosphine in carbon tetrachloride or triphenylphosphine and carbon tetrabromide in an organic solvent for example dichloromethane, chloroform, benzene.

We have found it convenient to carry out the conversion of an ester of a compound of the formula (X) to an ester of a compound of a formula (VI) in the same vessel. This is most conveniently performed by treating the ester of the compound of the formula (X) with a base at a temperature of from $-60°$ C. to 0° C., more suitably from $-50°$ C. to $-10°$ C. and preferably from $-40°$ C. to $-25°$ C. in an organic solvent such as chloroform or dichloromethane, and subsequently adding a solution of the imino-halogenating agent in an organic solvent whilst maintaining the reaction temperature at ambient temperature or below and then once the formation of the compound of the formula (IX) is substantially complete adding alcohol and base whilst maintaining the reaction temperature at 0° C. or below preferably between −30° C. and 0° C.; and then permitting the temperature to rise to ambient. The compound of the formula (VI) can be isolated by conventional methods such as chromatography, counter-current separation or crystallisation.

Esters of the compounds of the formula (X) may be prepared according to the methods defined in European Patent Publication No. 0004132, Japanese Application No. 25014/79, European Patent Application No. 79300517.4, United States Ser. No. 025,556 and Japanese Application No. 50233/79.

The compounds of the formulae (VI) and (IX) and as such form part of this invention.

In a further aspect the present invention provides a process for the preparation of a compound of the formula (XI):

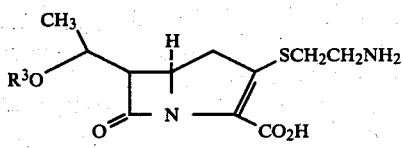

or a pharmaceutically acceptable salt or ester thereof wherein $R^3$ is as defined in relation to formula (II), with the proviso that the stereochemical configuration at the α-carbon atom of the C-6 substituent is S; and with the further proviso that when $R^3$ is a group $HO_3S$— the hydrogen atoms at C-5 and C-6 are cis; which process comprises the hydrolysis of a compound of the formula (VI) or salt or ester thereof; and thereafter if necessary:

(i) converting any cleavable ester group into a free acid, a pharmaceutically acceptable salt or different ester, (ii) removing any protecting groups.

Suitable protecting groups for $R^3$ when $R^3$ is hydrogen include tri $C_{1-4}$ alkylsilyl groups such as trimethylsilyl, and hydrogenolysable groups such as p-nitrobenzyloxycarbonyl. Suitably when $R^3$ is $HO_3S$— the compound of the formula (VI) is in the form of a tetra-substituted ammonium sulphate salt. Suitable the ester group is cleavable by chemical methods such as hydrogenation or hydrolysis, for example the p-nitrobenzyl and trimethylsilyl esters are preferred. Alternatively the ester group may be in-vivo hydrolysable for example the phthalidyl ester is preferred.

Suitably the hydrolysis is performed under neutral or acidic conditions for example using phosphate buffer at pH 7.

The following Examples illustrate the invention.

EXAMPLE 1 p-Nitrobenzyl (5R,6R)-3-(2-Phenylacetamidoethylthio)-6-[sodium(1S)-1-sulphonatooxyethyl]-7-oxo-1-azabicyclo[3.2.0]hept-2-ene-2-carboxylate

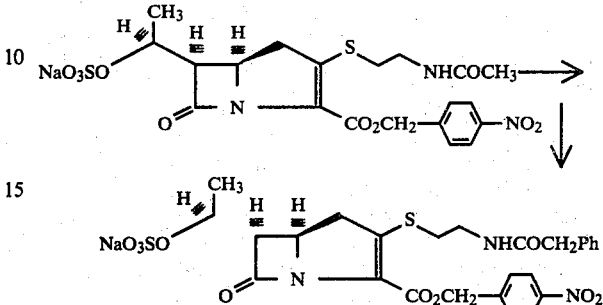

p-Nitrobenzyl (5R,6R)-3-(2-acetamidoethylthio)-6-[sodium(1S)-1-sulphonatooxyethyl]-7-oxo-1-azabicyclo[3.2.0]hept-2-ene-2-carboxylate (551 mg) was added to an aqueous solution (25 ml) of tetra-n-butylammonium hydrogen sulphate (170 mg) which had previously been neutralised to pH 7 with a 40% aqueous solution of tetra-n-butylammonium hydroxide. The resultant mixture was extracted with dichloromethane (3×50 ml) and the extract was dried (MgSO4) and evaporated in vacuo to give the tetra-n-butylammonium salt corresponding to the starting material [$\nu_{max}$ (CH2Cl2) 3440, 1780, 1700, 1670 cm$^{-1}$], toluene (20 ml) was added and evaporated in vacuo (2X) to remove any residual traces of moisture.

The tetra-n-butylammonium salt was then taken up in dry dichloromethane (15 ml), treated wth N-methylmorpholine (0.33 ml; 303 mg); cooled to −30° (internal temperature) and treated with a solution of PCl5 in dry dichloromethane (4.2 ml; 50 mg/ml). The solution was allowed to warm to −15° over 10 minutes when a further aliquot of the PCl5 solution (2.1 ml) was added. The mixture was then allowed to warm to 0° over ¾ hr., then recooled to −30° and N-methylmorpholine (1.0 ml, 920 mg) was added followed by anhydrous methanol (5.0 ml). The mixture was allowed to warm to 10° and stirred for 1.5 hr. The solution was then diluted to 50 ml with dichloromethane and then washed with an aqueous pH 7 buffer solution (2×20 ml), dried (MgSO4) and evaporated down to give the crude imino ether. The imino ether was dissolved in tetrahydrofuran (20 ml) containing an aqueous pH 7 buffer solution (2 ml) and palladium chloride (PdCl2) (92 mg) was added. After stirring for 1.5 hr. at ambient temperature, the tetrahydrofuran was evaporated in vacuo, ethanol (20 ml) added and evaporated in vacuo, toluene was added and evaporated in vacuo (3×30 ml). The residue was redissolved in dry dichloromethane (15 ml) and treated with pyridine (150 mg) followed by phenylacetyl chloride (154 mg). After 45 min. the dichloromethane was removed by evaporation in vacuo. The residue was redissolved in dichloromethane (100 ml) and washed with dilute aqueous NaHCO3 (50 ml), then with water (2×50 ml). The dichloromethane solution was dried (MgSO4) and stored overnight at −20°, then evaporated in vacuo and the residue chromatographed on silica gel (40 g, 0.040–0.063 mm) eluting with chloroform/ethanol mixtures; 8.2 (200 ml); 75:25 (100 ml); 7:3. The first major component (177 mg) to elute was the tetrabutylammonium salt of the phenylacetamide derivative [$v_{max}$ (CH$_2$Cl$_2$) 1780, 1705, 1670 cm$^{-1}$]. This was isolated by combination of the appropriate fractions and evaporation in vacuo. The tetrabutylammonium salt of the phenylacetamido derivative was taken up in acetone (2 ml) and treated with a solution of sodium iodide (40 mg) in acetone (1 ml). After trituration a solid deposited, this was filtered off and washed with acetone (1 ml) followed by ether (10 ml) and dried in a vacuum desiccator to give p-nitrobenzyl (5R,6R)-3-(2-phenylacetamidoethylthio)-6-[sodium(1S)-1-sulphonatooxyethyl]-7-oxo-1-azabicyclo[3.2.0]hept-2-ene-2-carboxylate (28 mg) $\lambda_{max}$ (H$_2$O) 315 (11,043), 274 (10,467); $v_{max}$ (KBr) 1770, 1695, 1650 cm$^{-1}$. δ [(CD$_3$)$_2$NDO] inter alia 1.49 (3H, d), 3.55 (2H, s), 5.31 and 5.56 (2H, ABq, J 14 Hz), 7.1–7.5 (5H, m), 7.82 (2H, d, J 9 Hz), 8.30 (3H, d, J 9 Hz, superposed on broad signal).

EXAMPLE 2

Disodium (5R,6R)-3-(2-Phenylacetamidoethylthio)-6-[(1S)-1-sulphonatooxyethyl]-7-oxo-1-azabicyclo[3.2.0]hept-2-ene-2-carboxylate

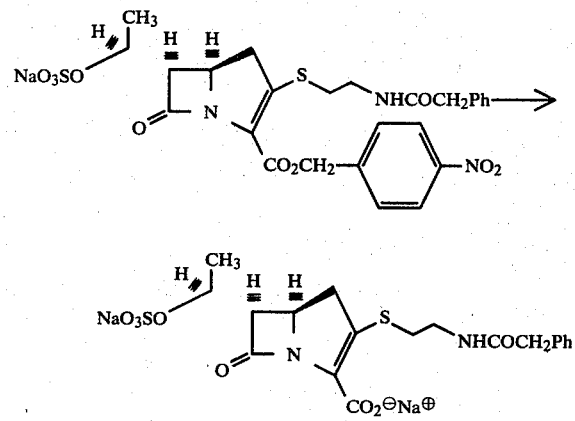

p-Nitrobenzyl (5R,6R)-3-(2-phenylacetamidoethylthio)-6-[sodium(1S)-1-sulphonatooxyethyl]-7-oxo-1-azabicyclo[3.2.0]hept-2-ene-2-carboxylate (8 mg) was added to prehydrogenated (15 min) 5% palladium on carbon catalyst (18 mg) in a mixture of dioxan (7 ml) and water (3 ml). The mixture was hydrogenated for 4½ hr., and then sodium hydrogen carbonate (2.0 mg) was added. The mixture was filtered through Celite, the filter cake was washed with water (10 ml). The volume of the combined filtrate and washings was reduced by evaporation in vacuo and the solution was then extracted with ethyl acetate.

After separation the aqueous solution was found to contain the desired disodium salt (4.8 mg), $\lambda_{max}$ 298 nm.

EXAMPLE 3 p-Nitrobenzyl (5R,6R)-3-(2-Phenoxyacetamidoethylthio)-6-[sodium(1S)-1-sulphonatooxyethyl]-7-oxo-1-azabicyclo[3.2.0]hept-2-ene-2-carboxylate

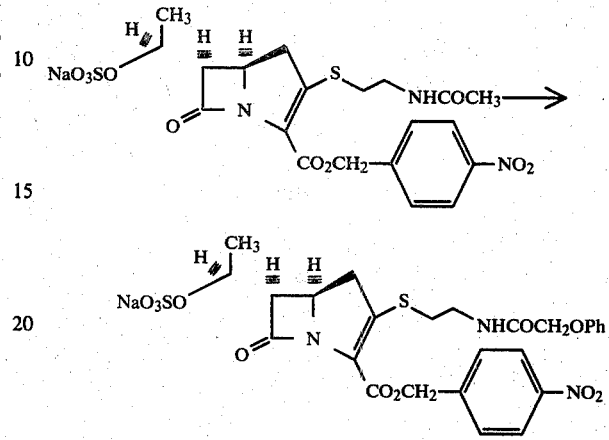

p-Nitrobenzyl (5R,6R)-3-(2-acetamidoethylthio)-6-[sodium(1S)-1-sulphonatooxyethyl]-7-oxo-1-azabicyclo[3.2.0]hept-2-ene-2-carboxylate (551 mg) was converted into the tetrabutylammonium salt as in Example A. This was taken up in dry dichloromethane (10 ml) and treated with N-methylmorpholine (1.0 ml; 0.92 g). The mixture was cooled to −30° (internal temperature) and a solution of PCl$_5$ in dry dichloromethane (18.9 ml) was added. The temperature of the reaction mixture was allowed to reach 10° over 45 min. to give a solution of the imino chloride ($v_{max}$ 1775, 1700 cm$^{-1}$). The solution was then recooled to −30°, N-methylmorpholine (3.0 ml; 2.76 g) was added followed by anhydrous methanol (7.5 ml). The mixture was allowed to warm to 10° over 30 min. and the temperature was then maintained at 10° for 1 hr. Dichloromethane (50 ml), aqueous pH 7 buffer solution (20 ml) and water (20 ml) were added, the layers separated and the dichloromethane layer was washed with aqueous pH 7 buffer solution (20 ml), dried (MgSO$_4$) and evaporated to give the crude imino ether ($v_{max}$ 1775, 1700, 1675 cm$^{-4}$).

Eight tenths of the crude imino ether product was taken up in dichloromethane (50 ml), and after keeping overnight at −20°, was treated at ambient temperature with p-toluenesulphonic acid monohydrate in ethyl acetate (3.0 ml 25 mg/ml). After 2 hrs. more of the p-toluenesulphonic acid monohydrate solution (3 ml) was added and stirring continued for a further 5 min. when pyridine (260 mg), followed by phenoxyacetyl chloride (136 mg), was added and the mixture stirred for 30 min. A further portion of phenoxyacetyl chloride (70 mg) was added and after stirring for a further 10 min. methanol (1 ml) was added to decompose any excess phenoxyacetyl chloride. The solution was washed with aqueous sodium hydrogen carbonate, then with aqueous pH 7 buffer solution, than with brine, then dried (MgSO$_4$) and evaporated to dryness.

The product was chromatographed on silica gel (30 g; 0.040–0.063 mm) eluting with chloroform (20 ml), followed by chloroform/ethanol mixtures; 8:2 (100 ml); 75:25 (100 ml); 7:3. Combination and evaporation of appropriate fractions (monitored by t.l.c.) gave slightly impure tetra-n-butylammonium salt of the phenoxyacetamide derivative (267 mg). This was dissolved in acetone (6 ml) and treated with sodium iodide (70 mg) in acetone (2 ml), a solid was deposited which was filtered off and washed with ether to give p-nitrobenzyl (5R,6R)-3-(2-phenoxyacetamidoethylthio)-6-[sodium(1S)-1-sulphonatooxyethyl]-7-oxo-1-azabicyclo[3.2.0]hept-2-ene-2-carboxylate (45 mg). $\lambda_{max}$ (H$_2$O) 316 (11900), 274 (11700), 268 (11600) nm; $\nu_{max}$ (KBr) 1770, 1690–1670 (broad) cm$^{-1}$. δ [(CH$_3$)$_2$NCDO] inter alia 1.49 (3H, d, J ~ 6 Hz), 4.55 (2H, s), 6.7–7.5 (5H, m), ppm.

EXAMPLE 4

Disodium (5R,6R)-3-(2-Phenoxyacetamidoethylthio)-6-[(1S)-1-sulphonatooxyethyl]-7-oxo-1-azabicyclo[3.2.0]hept-2-ene-2-carboxylate

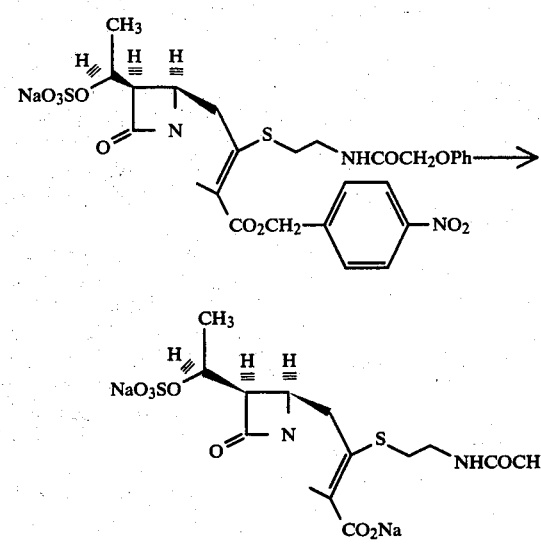

p-Nitrobenzyl (5R,6R)-3-(2-phenoxyacetamidoethylthio)-6-[sodium(1S)-1-sulphonatooxyethyl]-7-oxo-1-azabicyclo[3.2.0]hept-2-ene-2-carboxylate (31 mg) was added to prehydrogenated (30 min.) 5% palladium on carbon catalyst (54 mg) in a mixture of dioxan (7 ml) and water (3 ml).

The mixture was hydrogenated for 4.5 hr., and then sodium hydrogen carbonate (4.0 mg) was added and the mixture filtered through Celite. The filter cake was washed with water (20 ml) and the combined filtrate and washings were evaporated in vacuo to low volume. The solution was then loaded onto a column of Biogel P-2 (19×2.5 cm) and the column eluted with water. Fractions with a chromophore at ca. 300 nm were combined and reduced in volume by evaporation in vacuo, ca. two thirds of the solution was freeze dried to give disodium (5R,6R)-3-(2-phenoxyacetamidoethylthio)-6-[(1S)-1-sulphonatooxyethyl]-7-oxo-1-azabicyclo[3.2.0]hept-2-ene-2-carboxylate (12 mg) $\lambda_{max}$ (H$_2$O) 299, 274 and 267 nm. $\nu_{max}$ (KBr) 1755, 1660 and 1600 cm$^{-1}$.

EXAMPLE 5 p-Nitrobenzyl (5R,6R)-6-[(1)-1-Ethyloxysulphonyloxyethyl]-3-(2-phenoxyacetamidoethylthio)-7-oxo-1-azabicyclo[3.2.0]hept-2-ene-2-carboxylate

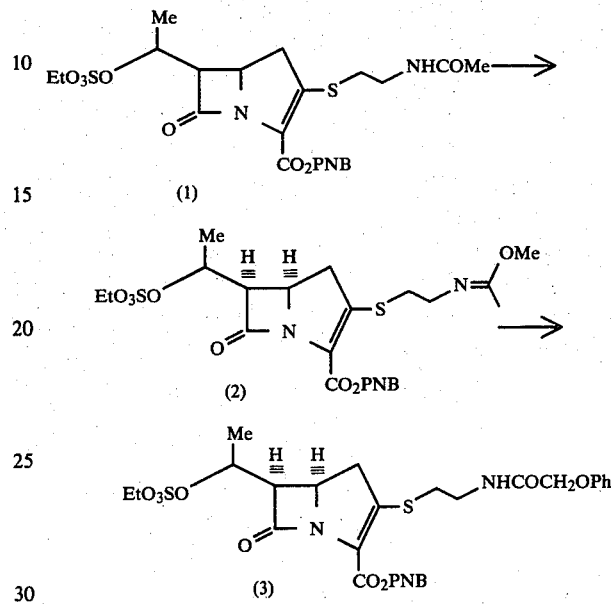

The diester (1) (0.55 g) was dissolved in dry dichloromethane (20 ml) and cooled to between −15° and −20°. N-methylmorpholine (0.202 g, 0.22 ml) was added followed by the dropwise addition over ca. 5 minutes of a solution of phosphorus pentachloride (5.3 ml of a solution containing 0.0585 g/ml). The solution was allowed to reach 0° over 45 minutes and then recooled to −20°. N-methylmorpholine (0.735 g, 0.8 ml) was then added followed by anhydrous methanol (5 ml). The mixture was allowed to warm to 10° and then poured with vigorous stirring into aqueous pH 7 buffer (20 ml). The mixture was partitioned and the organic phase separated, dried (MgSO$_4$) and evaporated to dryness. The residue was rapidly chromatographed through silica gel 60 (230–400 mesh ASTM) eluting with ethyl acetate. The imino-ether (2) (0.14 g) was obtained as a yellowish foam, $\lambda_{max}$ (EtOH) 267 nm and 318 nm; $\nu_{max}$ (CHCl$_3$) 1780, 1700, 1680, 1565, 1520 and 1350 cm$^{-1}$; δ ppm (CDCl$_3$) 1.45 (3H, t, J 7 Hz), 1.70 (3H, d, J 7 Hz), 1.90 (3H, s), 3.00–3.70 (6H, m), 3.63 (3H, s), 3.88 (1H, dd, J 10 and 6 Hz), 4.15–4.55 (1H, m), 4.37 (2H, q, J 7 Hz), 4.85–5.15 (1H, m), 5.23 and 5.52 (2H, ABq, J 14 Hz), 7.65 (2H, d, J 8 Hz), 8.25 (2H, d, J 8 Hz).

The imino-ether (2) (0.14 g) was dissolved in tetrahydrofuran (4 ml) and aqueous pH 7 buffer (0.4 ml) was added. Palladium chloride (0.027 g) was added and the mixture stirred for 45 minutes at R.T. The solution was then evaporated to dryness from toluene (X3) and the residue washed with hexane. The residual reddish solid was dissolved in dichloromethane (3 ml) and treated at R.T. with pyridine (0.039 g) followed by phenoxyacetyl chloride (0.042 g). After standing for 1 hour at R.T. the solution was washed with brine, dried (MgSO$_4$) and evaporated to dryness. The residue was chromatographed on silica gel 60 (230–400 mesh ASTM). Elution with 3/7 ethyl acetate/60°–80° petroleum ether followed by 1/1 ethyl acetate/60°–80° petroleum ether gave p-Nitrobenzyl (5R, 6R)-6-[(1S)-1-Ethyloxysulphonyloxyethyl]-3-(2-phenoxyacetamidoethylthio)-7-oxo-1-azabicyclo[3.2.0]hept-2-ene-2-carboxylate (3) as a solid (0.055 g), $\lambda_{max}$ (EtOH) 265 nm and 315 nm; $\lambda_{max}$ (CHCl$_3$) 3425, 1780, 1700, 1680, 1550, 1520 and 1350 cm$^{-1}$; δppm (CDCl$_3$) 1.45 (3H, t, J 7 Hz), 1.68 (3H, d, J 7 Hz), 3.00–3.65 (6H, m), 3.85 (1H, dd, J 10 and 6 Hz), 4.20–4.55 (1H, m), 4.38 (2H, q, J 7 Hz), 4.50 (2H, s), 4.85–5.20 (1H, m), 5.23 and 5.50 (2H, ABq, J 14 Hz), ca. 7 (1H, broad), 7.25–7.40 (5H, m), 7.62 (2H, d, J 8 Hz), 8.23 (2H, d, J 8 Hz).

Treatment with sodium iodide in dimethylformamide followed by hydrogenolysis as in example 4 affords the compound of example 4.

EXAMPLE 6 p-Nitrobenzyl (5R, 6R)-6-[(1S)-1-Ethyloxysulphonyloxyethyl]-3-(2-phenylacetamidoethylthio)-7-oxo-1-azabicyclo[3.2.0-]hept-2-ene-2-carboxylate

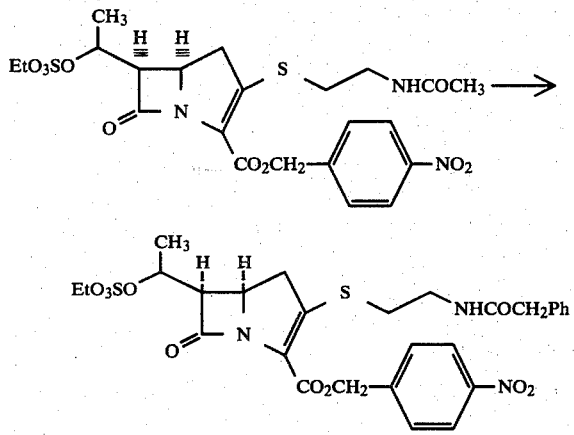

p-Nitrobenzyl (5R, 6R)-3-(2-acetamidoethylthio)-6-[(1S)-1-ethyloxysulphonyloxyethyl]-7-oxo-1-azabicyclo[3.2.0]hept-2-ene-2-carboxylate (110 mg) in dichloromethane (4 ml) was cooled to −15° (internal temperature) and N-methylmorpholine (0.044 ml; 42.6 mg) was added, followed by a solution of PCl$_5$ in CH$_2$Cl$_2$ (1.25 ml 50 mg/ml), added dropwise over ca. 0.5 min. The mixture was allowed to react 0° over ca. 30 min. and the resultant solution of the imino-chloride was recooled to −15° and N-methylmorpholine (0.16 ml; 155 mg) was added followed by anhydrous methanol (1.0 ml), added dropwise over 0.5 min. The mixture was allowed to warm to 5° to 10°, more N-methylmorpholine (0.04 ml) was added and the temperature was maintained between 5° and 10° for 30 min. when pH 7 aqueous buffer (4 ml) and CH$_2$Cl$_2$ (10 ml) were added and the mixture shaken and immediately separated. The dichloromethane layer was dried (MgSO$_4$) and evaporated in vacuo to give the imino ether. This was taken up in tetrahydrofuran (4 ml), pH 7 aqueous buffer solution (0.4 ml) was added followed by PdCl$_2$ (25 mg). The mixture was stirred at room temperature for 30 min., toluene (10 ml) was added to the mixture and the resultant mixture evaporated in vacuo. Toluene (20 ml) was added to the residue and evaporated in vacuo to leave the palladium complex of the amino compound as a gummy brown solid. This was suspended in dichloromethane (4 ml) and pyridine (32 mg) and phenylacetylchloride (31 mg) were added. After 30 min. the mixture was washed successively with aqueous NaHCO$_3$ solution, water and brine, and then dried (MgSO$_4$) and evaporated in vacuo. The residue was chromatographed on silica gel (15 g; 230–400 mesh ASTM) eluting with ethyl acetate/n-hexane mixtures: 70:30 (50 ml); 80:20 (50 ml); 90:10 (50 ml) and ethyl acetate. Collection and evaporation of the requisite fractions gave the phenyl acetyl derivative (17 mg), contaminated by hexane residues. The product was triturated under ether to give, after decantation, p-nitrobenzyl (5R, 6R)-6-[(1S)-1-ethyloxysulphonyloxyethyl]-3-(2-phenylacetamidoethylthio)-7-oxo-1-azabicyclo[3.2.0]hept-2-ene-2-carboxylate as a solid (8 mg) $\lambda_{max}$ (CH$_2$Cl$_2$) 3680, 3430, 1780, 1700, 1670 cm$^{-1}$ $\lambda_{max}$(EtOH) 315 and 264 nm. δ(CDCl$_3$) 1.41 (3H, t, J ca. 7 Hz), 1.67 (3H, d, J ca. 6 Hz), 2.75–3.50 (6H, m), 3.55 (2H, s), 3.83 (1H, dd, J 10 and 6 Hz), 4.0–4.6 (3H; q, centred at δ4.33, J ca. 7 Hz, superposed on m), 5.2 and 5.45 (2H, ABq, J ca 14 Hz), 5.80 (1H, broad s), 7.60 and 8.20 (each 2H, d, J 9 Hz).

Treatment with sodium iodide in dimethylformamide followed by hydrogenolysis as in example 2 affords the compound of example 2.

EXAMPLE 7 p-Nitrobenzyl (5R, 6R)-3-(2-Phenylacetamidoethylthio)-6-[benzyldimethyl-n-hexadecylammonium (1S)-1-sulphonatooxyethyl]-7-oxo-1-azabicyclo[3.2.0-]hept-2-ene-2-carboxylate

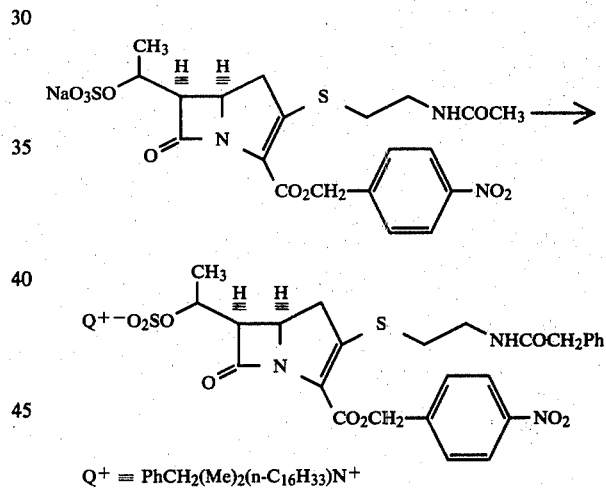

Q$^+$ = PhCH$_2$(Me)$_2$(n-C$_{16}$H$_{33}$)N$^+$ n-Nitrobenzyl (5R, 6R)-3-(2-acetamidoethylthio)-6-[sodium (1S)-1-sulphonatooxyethyl]-7-oxo-1-azabicyclo[3.2.0]hept-2-ene-2-carboxylate (500 mg) in water (10 ml) was shaken with benzyldimethyl-n-hexadecylammonium chloride in dichloromethane (20 ml). After separation (saturated aq. NaCl, 5 ml had been added to break up an emulsion) the dichloromethane layer was dried (MgSO$_4$) and evaporated to leave a gum, this was suspended in toluene (20 ml) and the toluene evaporated in vacuo (2X) to remove any residual traces of water, to leave the quaternary ammonium salt corresponding to the starting sodium salt. This was taken up in dry dichloromethane (20 ml), treated with N-methylmorpholine (0.25 ml; 230 mg), cooled to −15° (internal temperature) and then treated with a solution of PCl$_5$ in dichloromethane (6.4 ml; 43.8 mg/ml), which was added dropwise over 15 min. The mixture was allowed to reach 10° over 20 min. to give the imino chloride [$\lambda_{max}$ (CH$_2$Cl$_2$) 1780, 1710, 1670 cm$^{-1}$]. The solution was cooled to −20° and N-methyl morpholine (0.9 ml) was added, followed by anhydrous methanol (5.0 ml) and the mixture was then allowed to warm to 10° and stirred at 10° for 1 hr. The solution was diluted with dichloromethane (20 ml) and washed with aqueous pH 7 buffer solution (20 ml), followed by saturated aqueous NaCl (10 ml). The CH$_2$Cl$_2$ solution was dried

EXAMPLE 8 p-Nitrobenzyl (5R,6R)-3-[2-(5-Isothiazolylcarboxamido)ethylthio]-6-[tetra-n-butylammonium (1S)-1-sulphonatooxyethyl]-7-oxo-1-azabicyclo[3,2,0-]hept-2-ene-2-carboxylate.

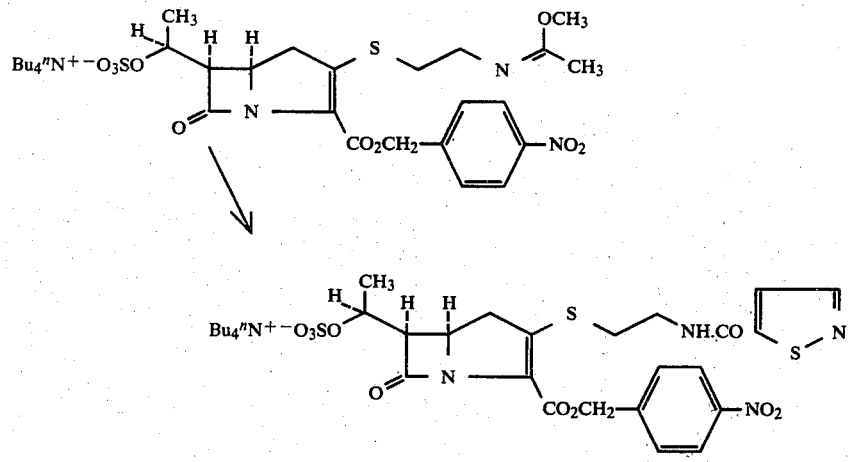

(MgSO$_4$) and evaporated in vacuo to give the crude imino ether, $\lambda_{max\ (CH_2Cl_2)}$ 1780, 1700, 1680 cm$^{-1}$. Nine tenths of this material was taken up in tetrahydrofuran (20 ml) containing PdCl$_2$ (86 mg) and aqueous pH 7 buffer solution (2 ml). The mixture was stirred until all the PdCl$_2$ had dissolved (ca. 1 hr.). The solution was evaporated in vacuo, ethanol (30 ml), was added and evaporated in vacuo (3X), toluene (20 ml) was added and evaporated in vacuo (3X), toluene (20 ml) was added and evaporated in vacuo (2X) and finally dichloromethane was added and evaporated in vacuo to leave the palladium complex of the amino compound. This was taken up in dichloromethane (20 ml) and treated with pyridine (150 mg) followed by phenylacetyl chloride (150 mg) and the mixture was stirred for 30 min. The mixture was then washed with aqueous NaHCO$_3$, followed by aqueous NaCl, dried (MgSO$_4$) and evaporated in vacuo to give the crude acylation product, this was purified by chromatography on silica gel (40 g; 1:1 mixture of 230–400 mesh ASTM and finer than 230 mesh ASTM) eluting with chloroform/ethanol mixtures: 90:10 (50 ml); 85:15 (100 ml); 80:20 (200 ml); 75:25 (100 ml); 70:30 (200 ml). Combination and evaporation of the appropriate fractions yielded the title compound as a gum; $\lambda_{max}$ (CH$_2$Cl$_2$) 1780, 1700, 1670 cm$^{-1}$; δ(CDCl$_3$) inter alia 1.70 (d, J 6 Hz, CH$_3$CH), 3.0 [s, (CH$_3$)$_2$ N$^+$>]3.48 (s, PhCH$_2$CO), 4.54 (s, PhCH$_2$+N<), 5.17 and 5.46 (2H, ABq, OCH$_2$Ar), 6.8–7.1 (m, exch. D$_2$O, NH), 7.22 (5H, s, C$_6$H$_5$), 7.44 (5H, s, C$_6$H$_5$), 7.61 (2H, d, J 9 Hz, 2×Ar-H), 8.18 (2H, d, J 9 Hz, 2×ArH).

Precipitation with sodium iodide from an acetone solution of the title compound yields the monosodium salt of example 2.

p-Nitrobenzyl (5R,6R)-3-(4-methoxy-3-azapent-3-en-1-ylthio)-6-[tetra-n-butylammonium (1S)-1-sulphonatooxyethyl]-7-oxo-1-azabicyclo[3.2.0]hept-2-ene-2-carboxylate (500 mg.) and palladium chloride (56 mg.) were stirred together in tetrahydrofuran (20 ml.) and pH 7 aqueous 0.1 M phosphate buffer solution (4 ml.). After stirring for 4 hrs. the solvents were removed by evaporation in vacuo. Ethanol (2×20 ml.) was added and evaporated in vacuo and then toluene (2×20 ml.) was added and evaporated in vacuo. The residue was taken up in dichloromethane and treated with pyridine (100 mg.) and 4-dimethylamino-pyridine (100 mg.), followed by 5-isothiazolylcarboxyl chloride (100 mg.). The mixture was mixture was stirred for 45 mins. and then more 5-isothiazolylcarboxyl chloride (30 mg.) was added and after 3 mins. the solution was washed with pH 7 aqueous 0.1 M phosphate buffer (20 ml), followed by water (20 ml.) and dilute brine (20 ml.). After drying the dichloromethane was removed by evaporation in vacuo and the residue chromatographed on silica gel (3×15 cm.), eluting with chloroform/ethanol mixtures; 9:1 (100 ml.); 85.15 (100 ml.); 80:20 (100 ml.), 70:30. Fractions containing the desired product were combined and evaporated in vacuo to leave p-nitrobenzyl (5R,6R)-3-[2-(5-isothiazolylcarboxamido)ethylthio]-6-[tetra-n-butylammonium (1S)-1-sulphonatooxyethyl]-7-oxo-1-azabicyclo[3.2.0]-hept-2-ene-carboxylate νmax (CH$_2$Cl$_2$) 1770, 1700, 1650 cm$^{-1}$.

EXAMPLE 9

Disodium Salt of (5R,6R)-3-[2-(5-Isothiazolyl-carboxamido)ethylthio]-6-[(1S)-1-hydroxysulphonyloxyethyl]-7-oxo-1-azabicyclo[3,2,0]hept-2-ene-2-carboxylic Acid

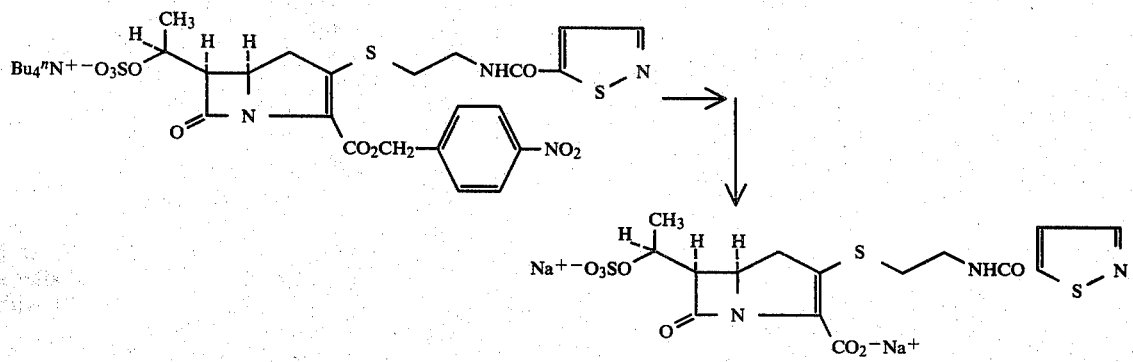

p-Nitrobenzyl (5R,6R)-3-[2-(5-isothiazolylcarboxamido)ethylthio]-6-[sodium (1S)-1-sulphonatooxyethyl]-7-oxo-1-azabicyclo[3,2,0]hept-2-ene-2-carboxylate (100 mg.) in dioxan (6 ml.)/water (3 ml.) and 5% palladium on carbon catalyst (150 mg.) were hydrogenated at atmospheric pressure for 2.25 hrs. Sodium hydrogen carbonate (10 mg.) in water (10 ml.) was added and the mixture was filtered through Celite and the filter cake washed with water (30 ml.). The volume of the filtrate was reduced to ca. 30 ml. by evaporation in vacuo and then extracted with ethyl acetate (4×150 ml.); sodium tetrafluoroborate (50 mg.) being added to the aqueous layer before the final wash. The volume of the aqueous solution was reduced to 10 ml. and the solution was chromatographed on Biogel P-2 (3×20 cm.), eluting with water. Fractions were monitored by u.v. spectroscopy and those containing a maximum at 297 nm were combined to give a solution containing the disodium salt of (5R,6R)-3-[2-(5-isothiazolylcarboxamido)ethylthio]-6-[(1S)-1-hydroxysulphonyloxyethyl]-7-oxo-1-azabicyclo[3.2.0]hept-2-ene-2-carboxylic acid.

EXAMPLE 10 p-Nitrobenzyl (5R,6R)-3-(2-propionamidoethylthio)-6-[sodium (1S)-1-sulphonatooxyethyl]-7-oxo-1-azabicyclo[3,2,0-]hept-2-ene-2-carboxylate.

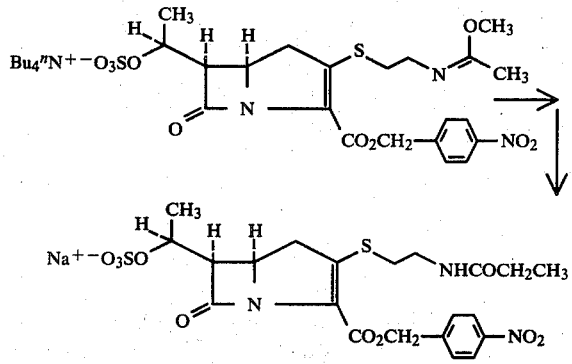

p-Nitrobenzyl (5R,6R)-3-(4-methoxy-3-azapent-3-en-1-ylthio)-6-[tetra-n-butylammonium (1S)-1-sulphonatooxyethyl]-7-oxo-1-azabicyclo[3,2,0]hept-2-ene-2-carboxylate (209 mg.) in tetrahydrofuran (10 ml.) and aqueous pH 7 buffer solution (2 ml.) was treated with palladium (II) chloride (24 mg.) and the mixture was stirred vigorously for 3¼ hrs., the solvents were then removed by evaporation in vacuo, ethanol (2×30 ml.) was added and removed in vacuo and then toluene (2×20 ml.) was added and evaporated in vacuo. The residual palladium complex of the amine was taken up in dry dichloromethane (10 ml.), treated with pyridine (25 mg.), 4-dimethylaminopyridine (33 mg.) followed by propionyl chloride (0.25 ml. 100 mg.ml$^{-1}$. solution in CH$_2$Cl$_2$) and the mixture was stirred for 1.25 hrs. Propionyl chloride (0.10 ml. 100 mg. ml.$^{-1}$ solution in CH$_2$Cl$_2$) was added and stirring was continued for 5 mins., when the solution was diluted to 30 ml. with dichloromethane and washed with water (2×20 ml.), followed by dilute brine (10 ml.). The dichloromethane layer was dried (MgSO$_4$) and evaporated to leave the crude tetra-n-butylammonium salt of the propionamido compound, νmax (CH$_2$Cl$_2$) 1775, 1700, 1600 cm$^{-1}$. This was taken up in acetone (5 ml.), treated with sodium iodide (80 mg.), and the acetone removed by evaporation in vacuo. The residue was chromatographed on silica gel (2.3×16 cm), eluting with CHCl$_3$/EtOH mixture; 9:1 (50 ml.), 8:2 (50 ml.), 7:3 (100 ml.), 6:4. The fractions were monitored by t.l.c. Fractions containing the desired sodium salt were collected, combined, and the solvents removed by evaporation in vacuo. The residue was triturated with acetone and the resultant solid filtered off to give p-Nitrobenzyl (5R, 6R)-3-(2-propionamidoethylthio)-6-[sodium (1S)-1-sulphonatooxyethyl]-7-oxo-1-azabicyclo[3,2,0]hept-2-ene-2-carboxylate (22 mg.), λmax (H$_2$O) 315 (εmax 13,012), 274 (max 11,177); δ (250 MHz) (D$_2$O) 0.87 (3H, t, J 7.5 Hz), 1.34 (3H, d, J ca. 6 Hz), 2.03 (2H, q, J ca. 7.5 Hz), 2.8–3.02 (2H, m), 3.11 (1H, dd, J 19 and 10.5 Hz), 3.23 (2H, approx t, J ca. 6 Hz), 3.37 (1H, dd, J ca. 19 and 8 Hz), 3.77 (1H, dd, J 8.5 and 6 Hz), 4.21 (1H, m), 5.11 and 5.23 (2H, ABq, J ca. 14 Hz), 7.42 (2H, d), 8.02 (2H, d) p.p.m.

EXAMPLE 11

Disodium Salt of (5R,6R)-3-(2-Propionamidoethylthio)-6-[(1S)-1-hydroxysulphonyloxyethyl]-7-oxo-1-azabicyclo[3,2,0-]hept-2-ene-2-carboxylic Acid

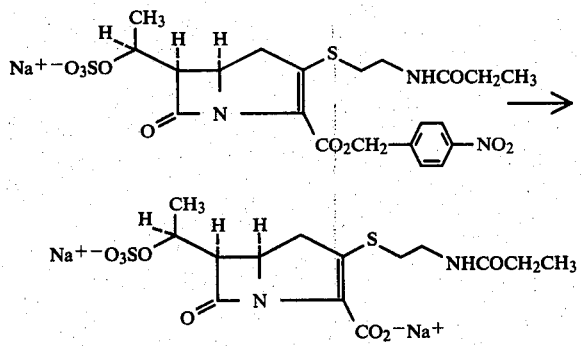

p-Nitrobenzyl (5R,6R)-3-(2-propionamidoethylthio)-6-[sodium (1S)-1-sulphonatooxyethyl]-7-oxo-1-azabicyclo[3,2,0]hept-2-ene-2-carboxylate (18 mg.) in water (3 ml.) and dioxan (6 ml.) was hydrogenated over 5% palladium on carbon catalyst (30 mg.) for 2¾ hrs. Sodium hydrogen carbonate (3 mg.) in water (2 ml.) was added and the mixture filtered through Celite. The filter cake was washed with water (20 ml.) and the combined filtrate and washings were evaporated in vacuo to ca. 20 ml., diluted with water (30 ml.), extracted with ethyl acetate (4×50 ml.), filtered, evaporated in vacuo to ca. 15 ml. and freeze-dried to give the disodium salt of (5R,6R)-3-(2-propionamidoethylthio)-6-[(1S)-1-hydroxysulphonyloxyethyl]-7-oxo-1-azabicyclo[3,2,0]-hept-2-ene-2-carboxylic acid, $\nu$max (KBr) 1750, 1655 (sh), 1570 (broad) cm$^{-1}$.

EXAMPLE 12 p-Nitrobenzyl (5R, 6R)-3-(2-[1-Phenoxycarbonyl-1-(3-thienyl]acetamidoethylthio)-6-[tetra-n-butylammonium (1S)-1-sulphonatooxyethyl]-7-oxo-1-azabicyclo[3,2,0-]hept-2-ene-2-carboxylate p-Nitrobenzyl (5R,6R)-3-(4-methoxy-3-azapent-3-en-1-ylthio)-6-[tetra-n-butylammonium (1S)-1-sulphonatooxyethyl]-7-oxo-1-azabicyclo[3,2,0]hept-2-ene-2-carboxylate (412 mg.) in tetrahydrofuran (20 ml.) and palladium (II) chloride (50 mg.) were treated with aqueous pH 7 buffer solution (4 ml.) and the mixture was stirred for 3½ hrs., the solvents were removed by evaporation in vacuo, ethanol (2×30 ml.) was added and removed in vacuo, and then toluene (2×20 ml.) was added and evaporated in vacuo. The residual palladium complex of the amine was taken up in dry dichloromethane and treated with pyridine (60 mg.) and 4-dimethylaminopyridine (66 mg.) followed by phenyl 3-thienylmalonyl chloride (150 mg.; prepared from the phenyl half ester of 3-thienylmalonic acid and oxalyl chloride in tetrahydrofuran containing a trace of N,N-dimethylformamide). After stirring the mixture for ¾ hr., more acyl chloride (15 mg.) was added and after a further 3 mins. the solution was diluted to 150 ml. with dichloromethane, washed with water (2×100 ml.), followed by dilute brine (50 ml.). The dichloromethane layer was dried (MgSO$_4$) and the solvent evaporated in vacuo. The residue was subsequently chromatographed on silica gel (2×3×15 cm), eluting with chloroform/ethanol mixtures; 100:0 (100 ml.), 95:5 (50 ml.), 90:10 (50 ml.), 85:15 (50 ml.); 80:20. Fractions containing the desired acylderivative were combined and evaporated in vacuo to give p-Nitrobenzyl (5R,6R)-3-{2-[1-phenoxycarbonyl-1-(3-thienyl)]-acetamidoethylthio}-6-[tetra-n-butylammonium (1S)-1-sulphonatooxyethyl]-7-oxo-1-azabicyclo[3,2,0]-hept-2-ene-2-carboxylate (89 mg.), $\nu$max (CH$_2$Cl$_2$) 1770, 1700, 1680 cm$^{-1}$, $\lambda$max (EtOH) 317, 266 nm.

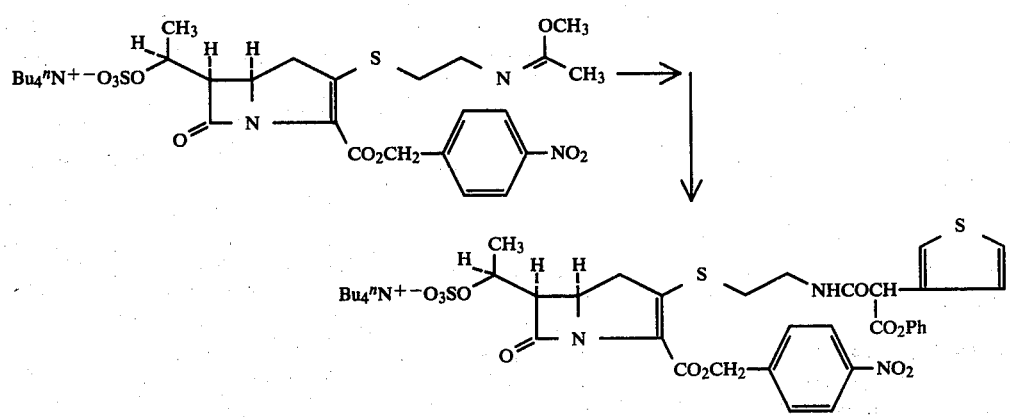

EXAMPLE 13

Disodium Salt of (5R,6R)-3-{2-[1-Phenoxycarbonyl-1-(3-thienyl)-]acetamidoethylthio}-6-[(1S)-1-hydroxysulphonyloxyethyl]-7-oxo-1-azabicyclo[3,2,0]-hept-2-ene-2-carboxylic Acid

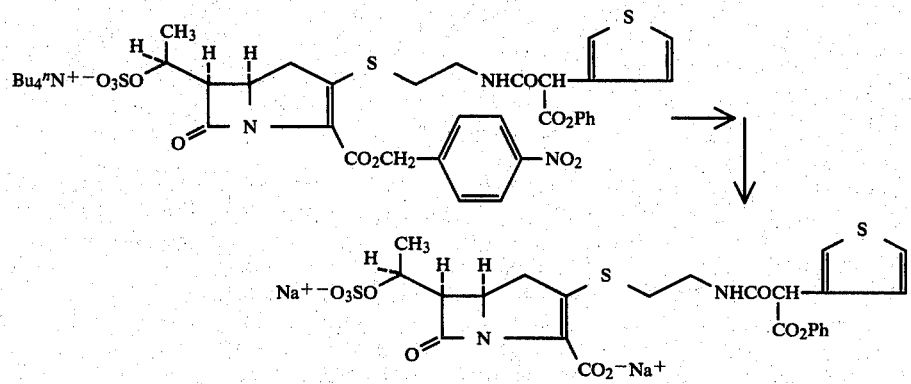

p-Nitrobenzyl (5R,6R)-3-{2-[1-phenoxycarbonyl-1-(3-thienyl)]acetamidoethylthio}-6-[tetra-n-butylammonium (1S)-1-sulphonatooxyethyl]-7-oxo-1-azabicyclo[3,2,0]hept-2-ene-2-carboxylate (80 mg.) in dioxan (6 ml.) and water (3 ml.) was hydrogenated over 5% palladium on carbon catalyst (100 mg.) for 2¾ hrs. Sodium hydrogen carbonate (8 mg.) was added, the mixture filtered through Celite, the filter cake was washed with water (20 ml.). The volume of the combined filtrate and washings was reduced by ca. ⅓ by evaporation in vacuo, and then diluted by water (20 ml.) containing sodium tetrafluoroborate (30 mg.), washed with dichloromethane (2×50 ml.), ethyl acetate (4×50 ml.), filtered through Celite, evaporated in vacuo to ca. 5 ml. and chromatographed on Biogel P-2 (2.3×14 cm.) eluting with water. The fractions were monitored by u.v. Fractions possessing the desired chromophore were combined, evaporated in vacuo to 10 ml. and then freeze-dried to give the disodium salt of (5R,6R)-3-{2-[1-phenoxycarbonyl-1-(3-thienyl)]acetamidoethylthio}-6-[(1S)-1-hydroxysulphonyloxyethyl]-7-oxo-1-azabicyclo[3,2,0]-hept-2-ene-2-carboxylic acid, $\nu_{max}$ (KBr) 1775, 1660, 1590 cm$^{-1}$.

EXAMPLE 14 p-Nitrobenzyl (5R,6R)-3-{2-[(R)-α-hydroxyphenyl-acetamidoethylthio]}-6-[sodium (1S)-1-sulphonatooxyethyl]-7-oxo-1-azabicyclo[3,2,0-]hept-2-ene-2-carboxylate

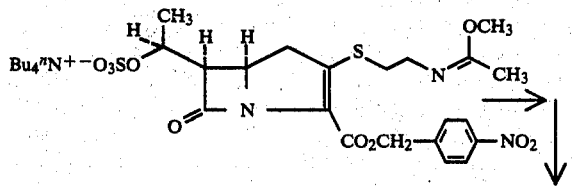

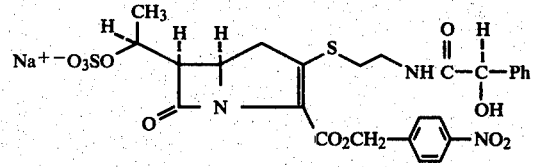

p-Nitrobenzyl (5R,6R)-3-(4-methoxy-3-azapent-3-en-1-ylthio)-6-[tetra-n-butylammonium (1S)-1-sulphonatooxyethyl]-7-oxo-1-azabicyclo[3,2,0]hept-2-ene-2-carboxylate (647 mg.) and palladium (II) chloride (74 mg.) were stirred together in tetrahydrofuran (30 ml.) and aqueous 0.1 M pH 7 phosphate buffer solution (6 ml.) for 2¾ hrs. The solvents were evaporated in vacuo, then ethanol (2×100 ml.) was added and removed in vacuo. Toluene (2×50 ml.) was added and removed by evaporation in vacuo to leave the crude palladium complex of the amine. This was dissolved in dichloromethane (20 ml.) and treated with pyridine (140 mg.) and 4-dimethylaminopyridine (120 mg.) followed by the cyclic anhydride (170 mg.), prepared by reaction of (R)-α-hydroxyphenylacetic acid [D(-)-mandelic acid] and phosgene. The mixture was stirred for 30 mins. and then diluted with dichloromethane (100 ml.), washed with water (2×50 ml.), then with dilute brine (20 ml.). After drying (MgSO₄) the dichloromethane was evaporated in vacuo and the residue chromatographed on silicon gel (2.3×14 cm.) eluting with chloroform/ethanol mixtures (25 ml. each of 0% EtOH, 10%, 15%, 20% and then 25% EtOH) to give the tetra-n-butylammonium salt of the acylated product (290 mg.), $\gamma_{max}$ (CH₂Cl₂) 1770, 1700, 1660 cm$^{-1}$. The salt was taken up in acetone (2 ml.) and treated with sodium iodide (70 mg.) in acetone (1 ml.). The acetone was evaporated in vacuo and the residue chromatographed on silica gel (2.3×14 cm.) eluting, as before with chloroform/ethanol mixtures (to 40% EtOH) to give the desired sodium salt, $\gamma_{max}$(KBr) 1770, 1690, 1650 cm$^{-1}$, contaminated by sodium iodide. The salt was rechromatographed on silica gel to give p-nitrobenzyl (5R,6R)-3-{2-[(R)-α-hydroxyphenyl-acetamidoethylthio]}-6-[sodium (1S)-1-sulphonatooxyethyl]-7-oxo-1-azabicyclo[3,2,0]hept-2-ene-2-carboxylate, $\lambda_{max}$ (H₂O) 315 ($\epsilon_{max}$ 10,777), 274 ($\epsilon_{max}$ 10,560) nm.; δ(250 MHz) [(CD₃)₂NCDO] 1.50 (3H, d, J ca. 6 Hz), 3.10 (2H,m), 3.2–3.4 (1H,m), 3.77 (1H,dd, J 5.5 11 Hz), 3.98 (1H, dd J ca. 9 and 19 Hz), 4.34 (1H,m), 4.59 (1H,m), 5.09 (1H,d, J ca. 6 Hz, S after D₂O exch.), 5.36 (1H,d, J ca. 15 Hz), 5.54 (1H,d, J ca. 15 Hz), 6.31 (1H,broad, exch.D₂O), 7.1–7.7 (3H,m), 7.50 (2H, approx d, J ca. 6 Hz), 7.83 (2H,d, J ca. 8 Hz), 8.30 (2H,d, J ca. 8 Hz), 8.40 (1H,m) ppm.

EXAMPLE 15

Disodium Salt of (5R,6R)-3-{2-[(R)-α-hydroxyphenylacetamidoethylthio]}-6-[(1S)-1-hydroxysulphonyloxy-ethyl]-7-oxo-1-azabicyclo[3,2,0]hept-2-ene-2-carboxylic Acid

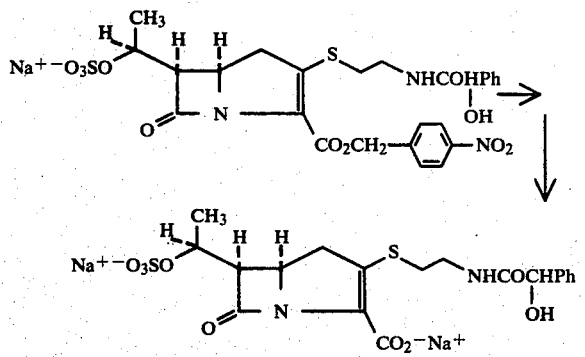

p-Nitrobenzyl (5R,6R)-3-{2-[(R)-α-hydroxyphenylacetamidoethylthio]}-6-[sodium (1S)-1-sulphonatooxyethyl]-7-oxo-1-azabicyclo[3,2,0]hept-2-ene-2-carboxylate (50 mg.) in dioxan (7 ml.)/water (3 ml.) containing 5% palladium on carbon catalyst (75 mg.) was hydrogenated at atmospheric pressure for 3 hrs. Sodium hydrogen carbonate (8 mg.) was added in water (2 ml.) and the solution filtered through Celite. The filter cake was washed with water (20 ml.) and the volume of filtrate and washings was reduced to ca. 15 ml. by evaporation in vacuo. The solution was then diluted with water (50 ml.) and extracted with ethyl acetate (3×50 ml.). The aqueous solution was again filtered through Celite and the volume of solution was reduced to ca. 40 ml. and freeze-dried to give the disodium salt of (5R,6R)-3-{2-[(R)-α-hydroxyphenylacetamidoethylthio]}-6-[(1S)-1-hydroxy-ethyl]-7-oxo-1-azabicyclo[3,2,0]hept-2-ene-2-carboxylic acid. $\gamma_{max}$ (KBr) 1750, 1650, 1590 cm$^{-1}$.

EXAMPLE 16 p-Nitrobenzyl (5R,6R)-3-(4-Methoxy-3-azapent-3-en-1-ylthio)-6-[tetra-n-butylammonium (1S)-1-sulphonatooxyethyl]-7-oxo-1-azabicyclo[3,2,0-]hept-2-ene-2-carboxylate

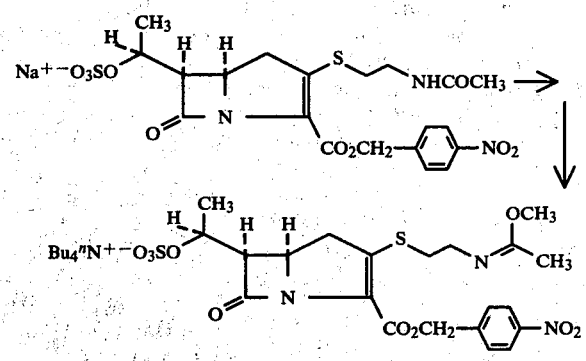

p-Nitrobenzyl (5R,6R)-3-(2-acetamidoethylthio)-6-[sodium(1S)-1-sulphonatooxyethyl]-7-oxo-1-azabicyclo[3,2,0]hept-2-ene-2-carboxylate (1.1 g.) in water (100 ml.) was treated with tetra-n-butylammonium sulphate [prepared from tetra-n-butylammonium hydrogen sulphate (340 mg.) by neutralisation to pH 7 with tetra-n-butylammonium hydroxide] in water (100 ml.) and the mixture was extracted with dichloromethane (4×100 ml.). The dichloromethane was dried (MgSO$_4$) and evaporated in vacuo. The residue was treated with toluene (2×50 ml.), which was removed by evaporation in vacuo to give the tetra-n-butylammonium salt corresponding to the starting sodium salt. The tetrabutylammonium salt was taken up in dry dichloromethane (15 ml.), treated with N-methylmorpholine (1.8 ml.), cooled to −30°, and treated with a solution of phosgene in toluene (3.5 ml., 12.5%, d 0.91).

The mixture was allowed to warm to ambient temperature, resulting in formation of the imidoyl chloride. The solution was recooled to −30° and treated with anhydrous methanol (5 ml.). The mixture was again allowed to warm to ambient temperature and stirred for 2 hrs., then diluted with dichloromethane (80 ml.) and then washed with water (3×100 ml.), dried (MgSO$_4$) and evaporated in vacuo to leave the methyl imidate, p-nitrobenzyl (5R,6R)-3-(4-methoxy-3-azapent-3-en-1-ylthio)-6-[tetra-n-butylammonium (1S)-1-sulphonatooxyethyl]-7-oxo-1-azabicyclo[3,2,0]-hept-2-ene-2-carboxylate, (1.3 g.), $\gamma_{max}$ (CH$_2$Cl$_2$) 1780, 1700, 1680 cm$^{-1}$.

EXAMPLE 17

Mono Sodium Salt of (5R,6R)-3-(2-aminoethylthio)-6-[(1S)-1-hydroxysulphonylethyl]-7-oxo-1-azabicyclo[3,2,0]-hept-2-ene-2-carboxylic Acid

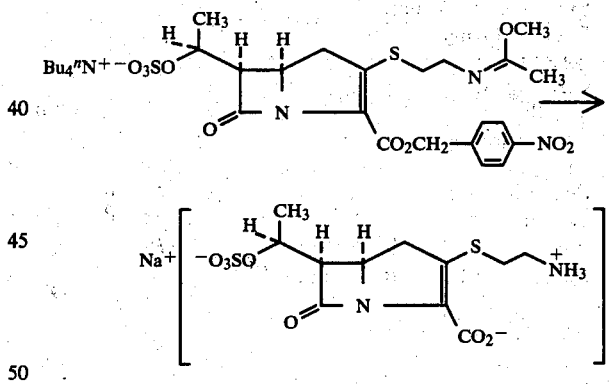

p-Nitrobenzyl (5R,6R)-3-(4-Methoxy-3-azapent-3-en-1-yl-thio)-6-[tetra-n-butylammonium (1S)-1-sulphonatooxyethyl]-7-oxo-1-azabicyclo[3,2,0]hept-2-ene-2-carboxylate (500 mg.) in dioxan (40 ml.) and pH 7 aqueous 0.1 M phosphate buffer solution (20 ml.) containing 5% palladium on carbon catalyst (750 mg.) was hydrogenated at atmospheric pressure for 2 hrs. The solution was then filtered through Celite and the filter cake washed with water (200 ml.). The combined filtrate and washings were reduced in volume to ca. 200 ml. by evaporation in vacuo and then extracted with ethyl acetate (4×250 ml.). The volume of the aqueous layer was then reduced to ca. 80 ml, treated with NaCl (4 g.) and loaded onto a column of DIAION HP-20 (3×18 cm.), and the column eluted with aqueous 5% NaCl solution (100 ml.), followed by deionised water. The fractions were monitored by u.v. spectroscopy and fractions containing a chromophore at 297 nm. were combined and freeze-dried to give the mono sodium salt of (5R,6R)-3-(2-aminoethylthio)-6-[(1S)-1-hydroxysulphonyloxyethyl]-7-oxo-1-azabicyclo[3,2,0]hept-2-ene-2-carboxylic acid (125 mg.), $\gamma_{max}$ 1750, 1590 cm$^{-1}$., $\lambda_{max}$ 296 ($\epsilon_{max}$ 5843)nm. (i.e. purity 68% assuming $\epsilon_{max}$ of pure material is 8,500).

EXAMPLE 18 p-Nitrobenzyl (5R,6S)-6-[(1S)-1-Hydroxyethyl]-3-(2-phenoxyacetamidoethylthio)-7-oxo-1-azabicyclo[3.2.0]hept-2-ene-2-carboxylate

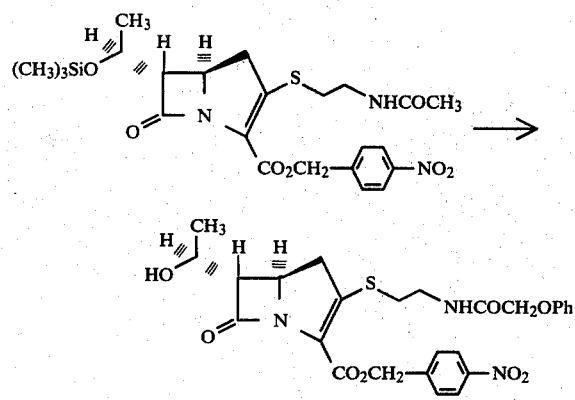

p-Nitrobenzyl (5R,6S)-3-(2-acetamidoethylthio)-6-[(1S)-1-trimethylsilyloxyethyl]-7-oxo-1-azabicyclo[3.2.0]hept-2-ene-2-carboxylate (117 mg) in dry dichloromethane (3.0 ml) was treated with N-methylmorpholine (0.05 ml, 46 mg), cooled to −30°, and treated with a solution of PCl$_5$ in dichloromethane (2.0 ml, 50 mg/ml). The mixture was then allowed to warm to 10° over 30 min. The mixture containing the imino-chloride was then recooled to −30° and N-methylmorpholine (0.60 ml, 550 mg) was added, followed by methanol (2.0 ml) which had been freshly distilled from anhydrous methanol over magnesium methoxide. The mixture was allowed to warm to 10° and the temperature maintained at 10° to 15° for 1.5 hr. Dichloromethane (10 ml) and aqueous pH 7 buffer solution (5 ml) were added and the mixture was shaken and separated. The dichloromethane layer was dried (MgSO$_4$) and evaporated to dryness in vacuo to give the imino-ether. This was taken up in tetrahydrofuran (10 ml) containing an aqueous pH 7 buffer solution (0.25 ml) and palladium (II) chloride (22 mg). After stirring at room temperature for 3 hr. the solvent was removed on a rotary evaporator, more tetrahydrofuran (5 ml) was added and evaporated in vacuo, and then ethanol (7 ml) was added and evaporated in vacuo followed by tetrahydrofuran (5 ml), followed by toluene (2×7 ml). The residual palladium complex of the amino-compound was suspended in dichloromethane (6 ml) containing pyridine (0.5 ml) and a solution of phenoxyacetylchloride in dichloromethane (0.38 ml; 100 mg/ml) was added. After stirring for 1 hr. another portion of the solution of phenoxyacetal chloride (0.1 ml) was added and stirring was continued for 3 min. when ethanol (2 ml) was added. After a further five minutes the solution was diluted with dichloromethane (30 ml) and washed with aqueous pH 7 buffer solution (20 ml). The dichloromethane layer was dried (MgSO$_4$) and evaporated in vacuo. The crude reaction product was chromatographed on silica gel (0.040-0.063 mm; 15 g) eluting with ethyl acetate/cyclohexane mixtures; 4:6; 1:1; 6:4; 7:3; 8:2; and 9:1 (25 ml of each mixture), followed by ethyl acetate (100 ml), followed by chloroform/ethanol 4:1. The chloroform/ethanol eluted the acyl compound (25 mg), this crystallised from dichloromethane to give p-nitrobenzyl (5R,6S)-6-[(1S)-1-hydroxyethyl]-3-(2-phenoxyacetamidoelthylthio)-7-oxo-1-azabicyclo[3.2.0]hept-2-ene-2-carboxylate (5 mg) m.p. 170°–172°; $\lambda_{max}$ (EtOH) 319 (12,900), 268 (12,700) nm, $\nu_{max}$ (KBr) 1775, 1695 and 1665 cm$^{-1}$.

Hydrogenolysis over 10% Palladiumon Carbon affords the sodium salt.

EXAMPLE 19

P-Nitrobenzyl (5R,6S)-6-[(1S)-1-Acetoxyethyl]-3-(2-phenoxyacetamidoethylthio)-7-oxo-1-azabicyclo[3.2.0]hept-2-ene-2-carboxylate

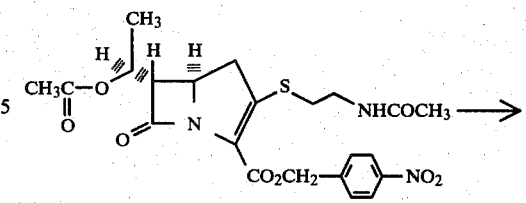

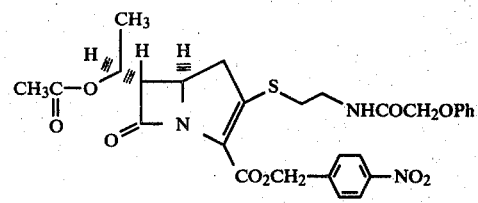

p-Nitrobenzyl (5R,6S)-6-[(1S)-1-acetoxyethyl]-3-(2-acetamidoethylthio)-7-oxo-1-azabicyclo[3.2.0]hept-2-ene-2-carboxylate (100 mg) in dry dichloromethane (4 ml) was treated with N-methylmorpholine (0.075 ml; 69 mg), cooled to −40° and PCl$_5$ in dichloromethane (2.0 ml 50 mg/ml) was added. The mixture was allowed to warm to 18°, then cooled to 0° when N-methylmorpholine (0.3 ml; 276 mg) was added and the mixture was then cooled to −30° when anhydrous methanol (3.0 ml) was added. The mixture was allowed to reach 15° over 30 min. and the temperature maintained at 10°–15° for a further 1 hr. The solution was diluted with dichloromethane (50 ml) and washed with pH 7 aqueous buffer solution (2×20 ml), dried (MgSO$_4$) and evaporated to leave the crude iminoether. This was taken up in dichloromethane (5 ml) and stirred vigorously with a solution of tetra-n-butylammonium hydrogen sulphate (70 mg). The progress of the hydrolysis was monitored by t.l.c., and as it appeared incomplete after 1 hr. more tetra-n-butylammonium hydrogen sulphate (70 mg) and stirring was continued for a further 30 min. The solution was diluted with water (20 ml) and dichloromethane (20 ml) were added, followed by a slight excess of aqueous sodium hydrogen carbonate. After shaking and separating the dichloromethane layer was dried (MgSO$_4$) and evaporated to leave the amino-compound. This was immediately taken up in dry dichloromethane (5 ml), treated with pyridine (0.5 ml) and phenoxyacetyl chloride (34 mg). After 10 min. ethanol (1 ml) was added followed by dichloromethane (20 ml). The mixture was washed with water (20 ml) and dried (MgSO₄) and evaporated. The i.r. of the crude material suggested incomplete acylation so the material was redissolved in dichloromethane (5 ml) containing pyridine (0.5 ml) and treated with phenoxyacetyl chloride (20 mg) for 10 min. Ethanol (0.5 ml) was then added and the mixture was worked up as before. Toluene (20 ml) was added and evaporated in vacuo to remove any residual pyridine and the product was then chromatographed on silica gel (15 g) eluting with ethyl acetate/cyclohexane (7:3) (50 ml), followed by ethyl acetate, to give p-nitrobenzyl (5R,6S)-6-[(1S)-1-acetoxyethyl]-3-(2-phenoxyacetamidoethylthio)-7-oxo-1-azabicyclo[3.2.0]hept-2-ene-2-carboxylate (18 mg), $\lambda_{max}$ 318, 275 (inf), 264, 261 (inf) nm; $\nu_{max}$ (CH₂Cl₂) 1785, 1735, 1700 (sh), 1685 cm⁻¹; δ(CDCl₃) 1.41 (3H, d, J 6 Hz), 2.09 (3H, s) 2.7–3.7 (7H, m), 3.75–4.25 (1H, m), 4.49 (2H, s), 5.0–5.6 (3H, m), 6.75–7.4 (6H, m) 7.60 (2H, d, J 9 Hz), 8.12 (2H, d, J 9 Hz) ppm.

EXAMPLE 20

Sodium (5R,6S)-6-[(1S)-1-Acetoxyethyl]-3-(2-phenoxyacetamidoethylthio)-7-oxo-1-azabicyclo[3.2.0]hept-2-ene-2-carboxylate

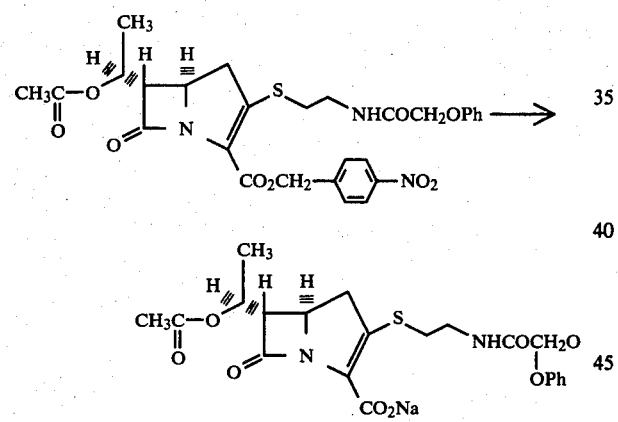

P-Nitrobenzyl (5R,6S)-6-[(1S)-1-acetoxyethyl]-3-(2-phenoxyacetamidoethylthio)-7-oxo-1-azabicyclo[3.2.0]hept-2-ene-2-carboxylate (10 mg) in dioxan (1 ml) was added to previously hydrogenated (15 min) 5% Pd/C catalyst in dioxan (7 ml)/water (3 ml) and the mixture was hydrogenated at atmospheric pressure for 4 hr. The catalyst was filtered off, the volume of solution reduced in vacuo, water (20 ml) was added and the resultant solution was washed with ethyl acetate, evaporated in vacuo to low volume and chromatographed on Biogel P-2 (15×2.3 cm) eluting with water. Fractions, monitored by u.v. spectroscopy, containing the sodium salt were combined and evaporated in vacuo to give sodium (5R,6S)-6-[(1S)-1-acetoxyethyl]-3-(2-phenoxyacetamidoethylthio)-7-oxo-1-azabicyclo[3.2.0]hept-2-ene-2-carboxylate as a solid, $\lambda_{max}$ (H₂O) 299, 276 (inf.), 265 (inf), 259 (inf).

EXAMPLE 21 p-Nitrobenzyl (5R,6S)-6-[(1S)-1-Hydroxyethyl]-3-(2-phenoxyacetamidoethylthio)-7-oxo-1-azabicyclo[3.2.0]hept-2-ene-2-carboxylate

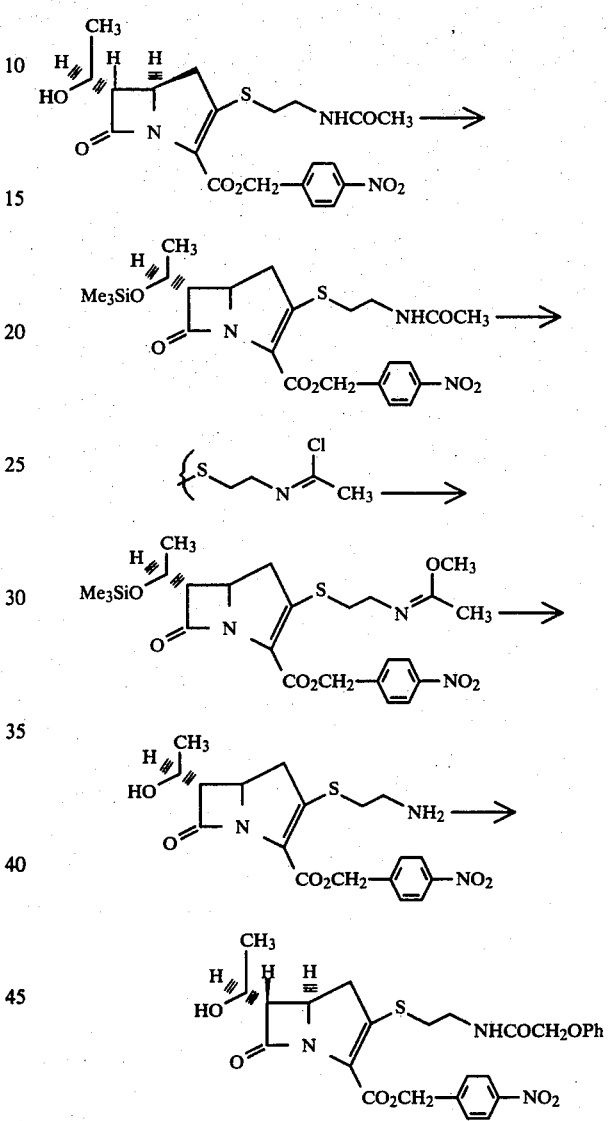

p-Nitrobenzyl (5R, 6S)-3-(2-acetamidoethylthio)-6-[(1S)-1-hydroxyethyl]-7-oxo-1-azabicyclo[3.2.0]hept-2-ene-2-carboxylate (250 mg) in pyridine (7 ml) was treated with aliquots of chlorotrimethylsilane (3×120 mg) until all the starting hydroxycompound had been consumed. The pyridine was evaporated in vacuo and the residue dissolved in ethyl acetate (20 ml) and water (10 ml). After separation the ethyl acetate was dried (MgSO₄) and evaporated in vacuo. Toluene was added to the residue and evaporated to leave the crude trimethylsilyl ether.

This was taken up in dry dichloromethane (10.0 ml) and treated with N-methylmorpholine (0.25 ml), cooled to −30° and treated with phosphorous pentachloride in dichloromethane (4.65 ml; 50 mg/ml). The mixture was allowed to warm to 10° and the temperature maintained at 10°–15° for 15 minutes.

The solution was then recooled to −30° and N-methylmorpholine (1.2 ml) was added followed by dry methanol (10 ml, freshly distilled from magnesium methoxide). The mixture was allowed to warm to 10° over 1 hour and the temperature maintained at 10°–18° over 1¾ hour. Dichloromethane (20 ml) and pH 7 aqueous buffer solution (20 ml) were added, the mixture shaken and separated and the dichloromethane layer was dried (MgSO$_4$) and evaporated to leave the iminoether as an oil. After standing at −16° for 3 days the oil had partially crystallized. These were isolated by addition of Et$_2$O/EtOAc and decantation, and then the crystals were washed with Et$_2$O and filtered off. The crystals (34 mg) proved to be p-nitrobenzyl (5R, 6S)-3-(4-methoxy-3-azapent-3-enylthio)-6-[(1S)-1-trimethylsilyloxyethyl]-7-oxo-1-azabicyclo[3.2.0]hept-2-ene-2-carboxylate, m.p. 115°–118°, δ (CDCl$_3$) 0.12 (9H, s), 1.28 (3H, d, J 6 Hz), 1.84 (3H, s), 2.8–4.4 (12H, m, including singlet at δ 3.55), 5.21 and 5.50 (2H, ABq, J 14 Hz), 7.64 (2H, d, J 9 Hz), 8.19 (2H, d, J 9 Hz); ν$_{max}$ (CH$_2$Cl$_2$) 1775, 1695, 1675 cm$^{-1}$; λ$_{max}$ (EtOH) 320 (11,950), 266 (10,960) cm$^{-1}$. Found M+ m/e 535.1807 C$_{24}$H$_{33}$N$_3$O$_7$SSi requires m/e 535.1808. The remaining iminoether from the supernatant liquours was taken up in dichloromethane (7 ml) and treated with tetra-n-butylammonium hydrogen sulphate in water (2 ml) and the mixture was stirred vigorously for 30 min. Excess aqueous NaHCO$_3$ was added, and the mixture diluted with dichloromethane (10 ml) and water (10 ml), and the layers were then separated and the dichloromethane layer was dried (MgSO$_4$) and evaporated to leave the crude amino-compound. This was taken up in CH$_2$Cl$_2$ (10 ml) and treated with pyridine (275 mg) followed by phenoxyacetylchloride (95 mg). After 20 min. phenoxyacetylchloride (10 mg) was added and after a further 2 min. the mixture was added to water (10 ml) and dichloromethane (10 ml) and the layers separated. The dichloromethane layer was dried (MgSO$_4$) and evaporated and the residue chromatographed on silica gel (20 g; 230–400 mesh ASTM), eluting with ethyl acetate cyclohexane mixtures; 7:3 (50 ml), 8:2 (50 ml); 9:1 (50 ml) then with ethyl acetate (100 ml) and then with ethylacetate/ethanol mixtures; 95:5 (50 ml), 9:1.

This yielded the phenoxyacetamido compound (29 mg) which crystallised on addition of dichloromethane to yield p-Nitrobenzyl (5R, 6S)-6-[(1S)-1-hydroxyethyl]-3-(2-phenoxyacetamidoethylthio)-7-oxo-1-azabicyclo[3.2.0]hept-2-ene-2-carboxylate (9 mg).

EXAMPLE 22

Sodium (5R,6S)-6-[(1S)-1-hydroxyethyl]-3-(2-phenoxyacetamidoethylthio)-7-oxo-1-azabicyclo[3.2.0]hept-2-ene-2-carboxylate

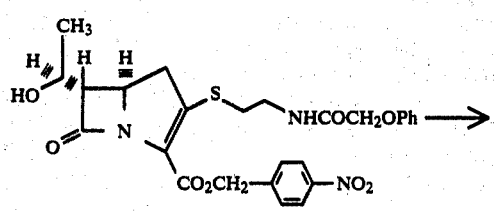

-continued

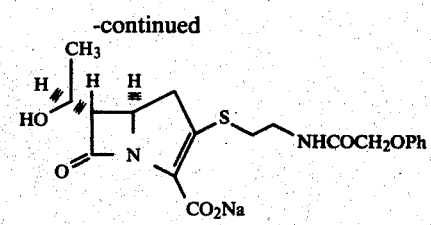

p-Nitrobenzyl (5R, 6S)-6-[(1S)-1-hydroxyethyl]-3-(2-phenoxyacetamidoethylthio)-7-oxo-1-azabicyclo[3.2.0]hept-2-ene-2-carboxylate (9 mg) was added to a suspension of prehydrogenated 5% Palladium on carbon catalyst (20 mg) in dioxan (7 ml) and water (3 ml). The mixture was hydrogenated at atmospheric pressure for 3.75 hr. Sodium hydrogen carbonate (7 mg) was added and the mixture was filtered through celite and the filter cake was washed with water (10 ml). The filtrate and washings were combined and evaporated in vacuo to ca. 2 ml, when water (10 ml) and ethyl acetate (10 ml) were added and the mixture was shaken and separated. The aqueous layer was evaporated in vacuo to dryness to leave the crude sodium salt. This was further purified by chromatography on Biogel P-2 (10×2.3 cm), eluting with water. The fractions were monitored by u.v. spectroscopy and those containing the chromophore corresponding to the sodium salt (λ$_{max}$ 391, 276, 265 inf.) were combined. Evaporation in vacuo to low volume, addition of ethanol followed by evaporation in vacuo (2X), followed by addition of toluene and evaporation in vacuo (2X) yielded sodium (5R, 6S)-6-[(1S)-1-hydroxyethyl]-3-(2-phenoxyacetamidoethylthio)-7-oxo-1-azabicyclo[3.2.0]hept-2-ene-2-carboxylate as a solid.

EXAMPLE 23 p-Nitrobenzyl (5R,6R)-3-(4-Methoxy-3-azapent-3-enylthio)-6-[(1S)-1-1-trimethylsilyloxyethyl]-7-oxo-1-azabicyclo[3.2.0]hept-2-ene-2-carboxylate

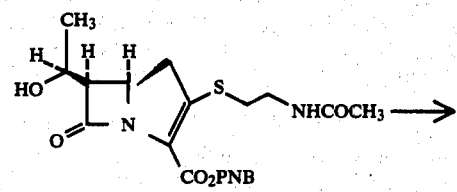

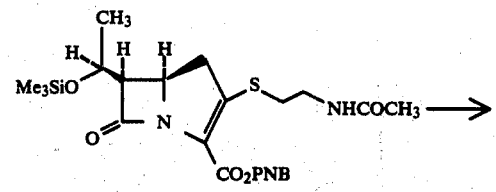

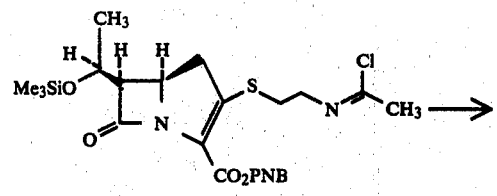

PNB≡CH$_2$C$_6$H$_4$NO$_2$(p)

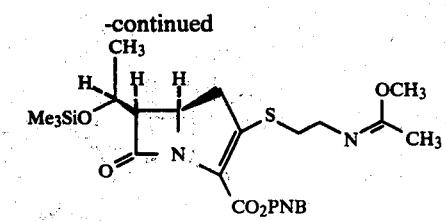

p-Nitrobenzyl (5R,6R)-3-(2-acetamidoethylthio)-6-[(1S)-1-hydroxyethyl]-7-oxo-1-azabicyclo[3.2.0]hept-2-ene-2-carboxylate (226 mg) in pyridine (3 ml) was treated with chlorotrimethylsilane (150 mg).

After stirring for 10 min., more chlorotrimethylsilane (150 mg) was added and stirring continued for a further 10 min. The pyridine was then removed by evaporation in vacuo and the residue taken up in ethyl acetate (50 ml) and washed with water (20 ml). The ethyl acetate was dried (MgSO$_4$) and evaporated to leave the silyl ether contaminated by a little pyridine. Residual traces of pyridine were removed by addition of toluene (20 ml) and evaporation in vacuo to leave the silyl ether, $v_{max}$ (CH$_2$Cl$_2$) 3450, 1780, 1700 (sh) and 1680 cm$^{-1}$. Trimethylsilyl ether was taken up in dry dichloromethane (10 ml) and N-methylmorpholine (0.50 ml) was added. The mixture was cooled to $-30°$ and a solution of phosgene in toluene (2.3 ml; 12.5% w/w) was added. The mixture was allowed to warm to ambient temperature over 30 min and the resultant solution containing the imino-chloride was treated with N-methylmorpholine (0.25 ml) and cooled to $-30°$. Dry methanol (4.0 ml) was added and the mixture was allowed to warm to 20°. After stirring for ¾ hr. the solution was diluted with dichloromethane (100 ml) and washed with aqueous pH 7 buffer solution (2×50 ml). The dichloromethane was dried (MgSO$_4$) and evaporated in vacuo to leave the title compound as an oil which crystallised on storage at $-16°$.

$\lambda_{max}$ (EtOH) 317 (11,430), 260 (11,110 nm); $v_{max}$ (CHCl$_2$) 1780, 1700, 1680 cm$^{-1}$. δ (CDCl$_3$) 0.12 (9H, s), 1.33 (3H, d, J 6 Hz), 1.84 (3H, s), 2.8–3.9 (10H, m, including s, 3H, at δ 3.57), 4.0–4.5 (2H, m), 5.21 and 5.49 (2H, ABq, J 14 Hz), 7.65 (2H, d, J 9 Hz), 8.21 (2H, d, J 9 Hz). Found M+ m/e 535.1803; C$_{24}$H$_{33}$N$_3$O$_7$SSi requires 535.1808).

EXAMPLE 24

(5R,6R)-3-(2-Aminoethylthio)-6-[(1S)-1-hydroxyethylthio]-7-oxo-1-azabicyclo[3.2.0]hept-2-ene-2-carboxylic acid

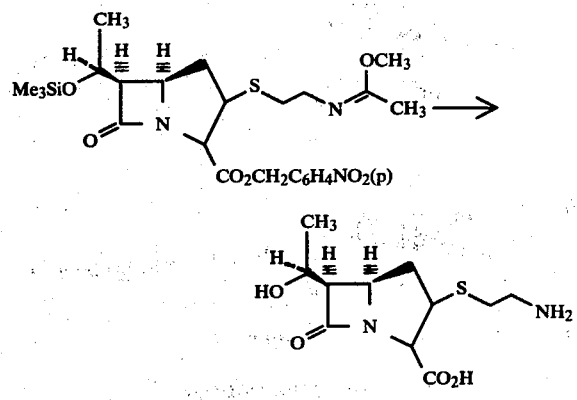

The product of Example 1 in dioxan (22.5 ml), ethanol (2.0 ml), water (7.0 ml) and M/20 pH 7 phosphate buffer solution (7.5 ml) was hydrogenated over 10% palladium on carbon catalyst (400 mg) at ca. atmospheric pressure for 2 hr. The catalyst was filtered off and washed with water (60 ml). The volume of combined filtrate and washings was reduced to ca. 30 ml by evaporation in vacuo, and the resultant mixture was washed with ethyl acetate (2×30 ml). The volume of the aqueous solution was then reduced to ca. 6 ml by evaporation in vacuo and the resultant solution was loaded onto a column of DIAION HP20 (2.5×12 cm) and eluted with water. Many fractions showed the desired u.v. chromophore at 296 nm, these were combined and u.v. assay of the solution indicated the presence of ca. 40 mg of the desired compound, indicating a yield of ca. 30% from the starting p-nitrobenzyl (5R,6R)-3-(2-acetamidoethylthio)-6-[(1S)-1-hydroxyethyl]-7-oxo-1-azabicyclo[3.2.0]hept-2-ene-2-carboxylate.

Some of the solution was freeze dried to give the title compound as a cream coloured solid, $\lambda_{max}$ (H$_2$O) 296, $v_{max}$ (KBr) 1750, 1605 cm$^{-1}$. δ (D$_2$O, CH$_3$CN internal standard at δ 1.27 (d, J 6 Hz, CH$_3$CH), 2.6–3.4 (m, SCH$_2$CH$_2$N, 4-CH$_2$), 3.59 (dd, J 6 and 10 Hz, 6-CH), 3,8–4.5 (m, 5-CH, 8-CH).

EXAMPLE 25 p-Nitrobenzyl (5R,6R)-3-[2-(isothiazolyl-4-carboxamidolethylthio]-6-[(S)-1-trimethylsilyloxyethyl]-7-oxo-1-azabicyclo[3.2.0-]hept-2-ene-2-carboxylate

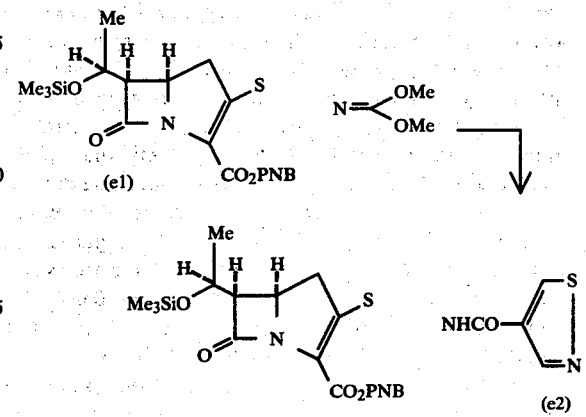

A solution of the imidate (e1) (500 mg) in dry THF (25 ml) was stirred with palladium chloride (83 mg) at room temperature for 2.5 h. The solution was concentrated to dryness and was then evaporated down from ethanol (2×25 ml) and finally toluene (3×25 ml). The residue was dissolved in dry dichloromethane (30 ml) and to the solution was added pyridine (73 mg) and 4-dimethylaminopyridine (114 mg) followed by isothiazole-4-carbonyl chloride (0.33 ml of a 3 mM solution in CH$_2$Cl$_2$). The solution was stirred for 30 min at room temperature and was then diluted with dichloromethane (20 ml). The organic solution was washed with 0.05 M pH 7 phosphate buffer (30 ml), water (30 ml) and brine (20 ml). Evaporation of the dried organic layer (MgSO$_4$) gave a residue which was chromatographed on a column of silica-gel using a gradient elution of 50% petroleum ether (60°-80°)-ethyl acetate to neat ethyl acetate.

The title compound (e2) was obtained as a foam; λ$_{max.}$ (EtOH) 317 and 262 nm., ν$_{max.}$ (CH$_2$Cl$_2$) 3460, 1780, 1710 and 1670 cm$^{-1}$; δ (CDCl$_3$) 0.09 (9H, s, Me$_3$Si) 1.34 (3H, d, J Hz, MeCH), 3.00–3.25 (3H, m, C$\underline{H}_2$S and 4-CHa), 3.57–3.80 (4H, m, 4-CHb, 6-CH and NCH$_2$), 4.28 (2H, m, 5-CH and C$\underline{H}$Me), 5.23 and 5.48 (each 1H, d, J 14 Hz, C$\underline{H}_2$Ar), 6.70 (1H, br, NH), 7.64 and 8.20 (each 2H, d, J 9 Hz, C$_6$H$_4$-NO$_2$), 8.81 and 9.10 (each 1H, s, isothiazole-CH).

EXAMPLE 26

Sodium (5R,6R)-3-[2-(isothiazolyl-4-carboxamido)ethylthio]-6-[(S)-1-hydroxyethyl]-7-oxo-1-azabicyclo[3.2.0]hept-2-ene-2-carboxylate

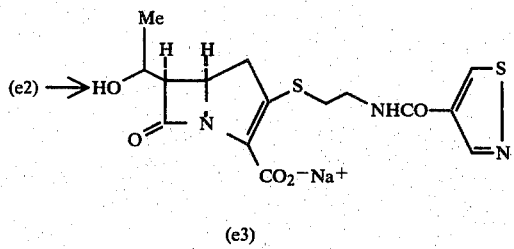

(e3)

A solution of the ester (e2) (15 mg) in 30% aqueous dioxan (8 ml) was hydrogenated in the presence of 5% Pd on C (22 mg) at ambient temperature and pressure for 2 hours. Sodium bicarbonate (3 mg) was added to the mixture which was then filtered over Celite, washing the pad with water (20 ml). The aqueous solution was washed with ethyl acetate (3×25 ml) and then concentrated to small volume. The solution was chromatographed on a column of Biogel P2 (10×2.5 cm) eluting with water to afford the title sodium salt (e3); λ$_{max.}$ (H$_2$O) 295 and 254 cm$^{-1}$.

EXAMPLE 27

P-Nitrobenzyl (5R,6R)-3-(2-Phenoxyacetamidoethylthio)-6-[(1S)-1-trimethylsilyloxyethyl]-7-oxo-1-azabicyclo[3.2.0]hept-2-ene-2-carboxylate

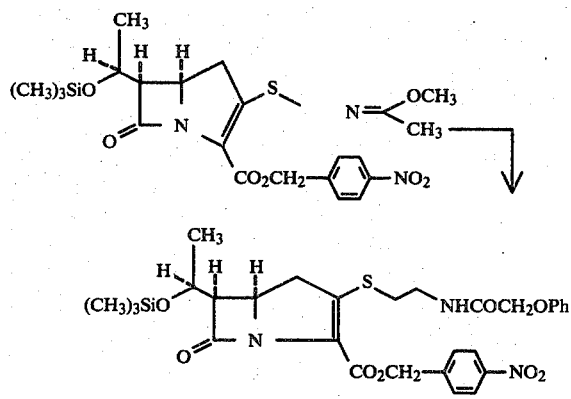

P-Nitrobenzyl (5R,6R)-3-(4-methoxy-3-azapent-3-en-1-yl-thio)-6-[(1S)-1-trimethylsilyloxyethyl]-7-oxo-1-azabicyclo[3.2.0]hept-2-ene-2-carboxylate (266 mg) was dissolved in tetrahydrofuran (5 ml) and pH 7 0.1 M aqueous phosphate buffer solution (0.5 ml) was added, followed by palladium chloride (44 mg). The mixture was stirred vigorously for 1.5 hr. and the solvents were then removed by evaporation in vacuo. Toluene (4×10 ml) was added to the residue and removed by evaporation in vacuo. The residue was then suspended in dry dichloromethane (5 ml) and treated with 4-dimethylaminopyridine (65 mg), followed by phenoxyacetyl chloride (85 mg). After 30 minutes the solution was diluted to 50 ml by addition of dichloromethane and the solution was washed successively with pH 7 0.1 M aqueous phosphate buffer solution (2×25 ml), brine (50 ml), then dried (MgSO$_4$) and evaporated in vacuo.

The product was chromatographed on silica gel (20 g), eluting with ethyl acetate/cyclohexane mixtures; 1:1 (25 ml), 6:4 (25 ml), 7:3 (25 ml), 8:2 (25 ml), 9:1 (25 ml) and then with ethyl acetate. Fractions containing the desired acylated material were combined and evaporated to leave p-nitrobenzyl (5R,6R)-3-(2-phenoxyacetamidoethylthio)-6-[(1S)-1-trimethylsilyloxyethyl]-7-oxo-1-azabicyclo[3.2.0]-hept-2-ene-2-carboxylate (76 mg), ν$_{max.}$ (CH$_2$Cl$_2$) 3430, 1780, 1700 (Sh), 1685, 1525, 1350, 1335, 1135, 845 cm$^{-1}$., δ (CDCl$_3$) 0.12 (9H, s), 1.34 (3H, d, J 6 Hz), 2.9–3.3 (3H, m), 3.50–3.66 (3H, m), 3.75 (1H, dd, J 17.5 and 9 Hz), 4.2–4.4 (2H, m), 4.49 (2H, s), 5.25 and 5.49 (2H, each d, J 14 Hz), 6.91 (2H, d, J 8 Hz), 6.96–7.10 (3H, approx t), 7.32 (2H, t, J 8 Hz), 7.86 (2H, d, J 9 Hz), 8.21 (2H, d, J 9 Hz). [Found M+ m/e 613.1894; C$_{29}$H$_{35}$N$_3$O$_8$SSi requires m/e 613.1913].

EXAMPLE 28

Sodium (5R,6R)-6-[(1S)-1-Hydroxyethyl]-3-(2-phenoxyacetamido)-7-oxo-1-azabicyclo[3.2.0]hept-2-ene-2-carboxylate

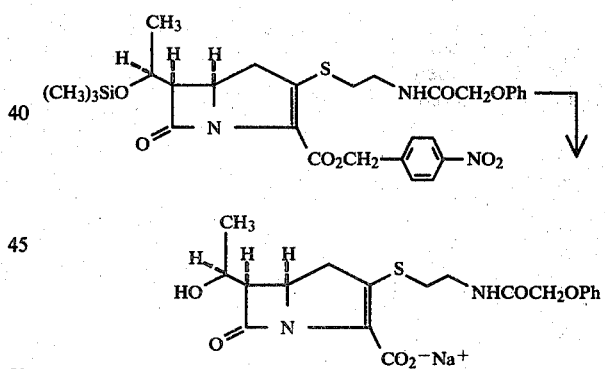

P-Nitrobenzyl (5R,6R)-3-(2-phenoxyacetamidoethylthio)-6-[(1S)-1-trimethylsilyloxyethyl]-7-oxo-1-azabicyclo[3.2.0]hept-2-ene-2-carboxylate (110 mg) was added to 5% palladium on carbon catalyst (190 mg) in dioxan (23 ml) and water (9 ml). The mixture was hydrogenated for 3½ hrs and then treated with sodium hydrogen carbonate (16 mg) and then filtered through Celite. The filter cake was washed well with water and the filtrate and washings were evaporated in vacuo to lower volume and the resultant solution was washed with ethyl acetate (2×100 ml). The volume of the aqueous solution was reduced by evaporation in vacuo and freeze dried to give sodium (5R,6R)-6-[(1S)-1-hydroxyethyl]-3-(2-phenoxyacetamido)-7-oxo-1-azabicyclo[3.2.0.-]hept-2-ene-2-carboxylate. λ$_{max.}$ (H$_2$O) 299, 276, 270, 264 nm; λ$_{max.}$ (KBr) 1750, 1655 cm$^{-1}$.

EXAMPLE 29

P-Nitrobenzyl (5R,6R)-3-(4-Ethoxy-3-azapent-3-en-1-yl-thio)-6-[(1S)-1-trimethylsilyloxyethyl]-7-oxo-1-azabicyclo[3.2.0-]hept-2-ene-2-carboxylate

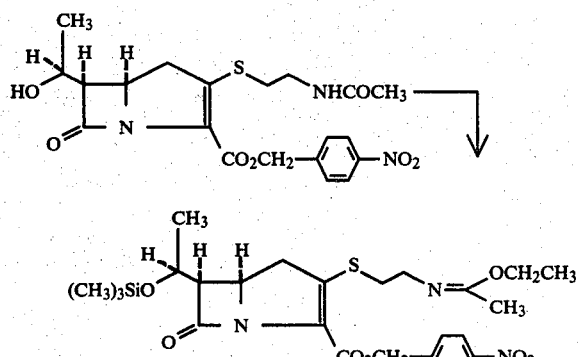

P-Nitrobenzyl (5R,6R)-3-(2-acetamidoethylthio)-6-[(1S)-1-hydroxyethyl]-7-oxo-1-azabicyclo[3.2.0]hept-2-ene-2-carboxylate (175 mg) in pyridine (2 ml) was treated with chlorotrimethylsilane (300 mg). After 30 min the pyridine and excess chlorotrimethylsilane were removed by evaporation in vacuo and ethyl acetate (50 ml) and water (30 ml) were added. The layers were separated and the ethyl acetate layer was washed with water (30 ml), followed by brine (20 ml), then dried (MgSO₄) and evaporated to leave the silyl ether contaminated by traces of pyridine. The pyridine was removed by addition and evaporation in vacuo of toluene (20 ml).

The silyl ether was taken up in dry dichloromethane (5 ml), treated with N-methylmorpholine (0.50 ml; 460 mg) and cooled to −30° and then treated with a solution of phosgene in toluene (0.75 ml 12.5% α 0.91). The mixture was then allowed to warm to room temperature and stirred for 15 minutes and then recooled to −30° and treated with anhydrous ethanol (4 ml). The mixture was then allowed to warm to room temperature and stirred for 1.5 hours. The solution was then diluted to 50 ml with CH₂Cl₂ and washed with pH 7 aqueous buffer solution (2×50 ml), then with brine (20 ml), and then dried (MgSO₄) and evaporated to dryness to give p-nitrobenzyl (5R,6R)-3-(4-ethoxy-3-azapent-3-en-1-ylthio)-6-[(1S)-1-trimethylsilyloxyethyl]-7-oxo-1-azabicyclo[3.2.0.]hept-2-ene-2-carboxylate, $v_{max}$. (CH₂Cl₂) 1780, 1700, 1675 cm⁻¹.

DESCRIPTION 1 p-Nitrobenzyl (5R,6S)-3-(2-Acetamidoethylthio)-6-[(1S)-1-trimethylsilyloxyethyl]-7-oxo-1-azabicyclo[3.2.0]hept-2-ene-2-carboxylate

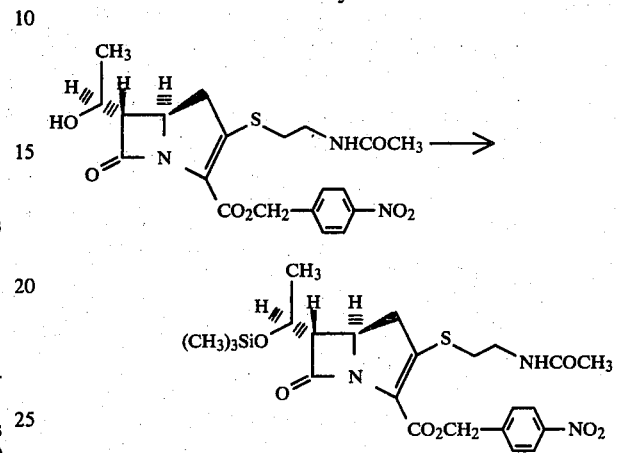

p-Nitrobenzyl (5R,6S)-3-(2-acetamidoethylthio)-6-[(1S)-1-hydroxyethyl]-7-oxo-1-azabicyclo[3.2.0]hept-2-ene-2-carboxylate (250 mg) in pyridine (7 ml) were treated with 70 mg. aliquots of chlorotrimethylsilane until all the starting hydroxycompound has reacted (4 aliquots required). The pyridine was removed by evaporation in vacuo, ethyl acetate (20 ml) was added to the residue and the resultant solution washed with water (20 ml). The ethyl acetate was dried (MgSO₄) and evaporated in vacuo. Toluene (20 ml) was added to the residue and evaporated in vacuo to remove residual traces of pyridine. The crude silyl ether was then chromatographed on silica gel (0.040–0.063 mm; 15 g) eluting with ethyl acetate. Fractions containing the trimethylsilyl ether were combined and evaporated in vacuo to yield p-nitrobenzyl (5R, 6S)-3-(2-acetamidoethylthio)-6-[(1S)-1-trimethylsilyloxyethyl]7-oxo-1-azabicyclo[3.2.0]hept-2-ene-2-carboxylate (145 mg). Found M⁺ m/e 521.1657 C₂₃H₃₁N₃O₇SSi requires m/e 521.1650.

| | DEMONSTRATION OF EFFECTIVENESS | | | | | |
|---|---|---|---|---|---|---|
| | COMPOUND OF EXAMPLE | | | | | |
| ORGANISM | 18 | 15 | 11 | 13 | 26 | 9 |
| *Citrobacter freundii* E8 | 8.0 | 8.0 | 4.0 | 125 | 3.1 | 0.8 |
| *Enterobacter cloacae* N1 | 16 | 2.0 | 1.0 | 31 | 3.1 | 0.8 |
| *Escherichia coli* O111 | 16 | 2.0 | 2.0 | 16 | 0.8 | 0.4 |
| *Escherichia coli* JT 39 | 31 | 1.0 | 0.2 | 8.0 | 6.2 | 0.2 |
| *Klebsiella aerogenes* A | 16 | 0.5 | 0.5 | 8.0 | 0.8 | 0.2 |
| *Proteus mirabilis* C977 | 31 | 2.0 | 0.5 | 4.0 | 0.4 | 0.2 |
| *Proteus morganii* 1580 | 8.0 | 1.0 | 2.0 | 8.0 | 6.2 | 0.8 |
| *Proteus rettgeri* WM16 | 16 | 2.0 | 1.0 | 16 | 3.1 | 0.4 |
| *Proteus vulgaris* WO91 | 16 | 1.0 | 1.0 | 16 | 6.2 | 0.8 |
| *Pseudomonas aeruginosa* A | >250 | 250 | >250 | 250 | 100 | 100 |
| *Salmonella typhimurium* CT10 | 16 | 1.0 | 1.0 | 16 | 0.8 | 0.8 |
| *Serratia marcescens* US20 | 62 | 4.0 | 4.0 | 62 | 3.1 | 1.6 |
| *Shigella sonnei* MB 11967 | 31 | 1.0 | 2.0 | 31 | 0.8 | 0.4 |
| *Bacillus subtilis* A | 1.0 | ≦0.2 | 1.0 | 2.0 | 0.2 | 0.2 |
| *Staphylococcus aureus* Oxford | 4.0 | 4.0 | 2.0 | 8.0 | 0.4 | 0.8 |
| *Staphylococcus aureus* Russell | 4.0 | 4.0 | 4.0 | 2.0 | 0.8 | 1.6 |
| *Staphylococcus aureus* 1517 | 4.0 | 31 | 250 | 125 | 12.5 | 25 |
| *Streptococcus faecalis* I | 62 | 31 | 31 | 62 | 0.8 | 3.1 |

-continued
DEMONSTRATION OF EFFECTIVENESS

| | | | | | | |
|---|---|---|---|---|---|---|
| Streptococcus pneumoniae CN33 | 1.0 | 1.0 | ≦0.2 | 2.0 | ≦0.1 | 0.2 |
| Streptococcus pyogenes CN 10 | 0.5 | 0.5 | ≦0.2 | 2.0 | 0.2 | 0.2 |
| E.coli ESS | 8.0 | 2.0 | ≦0.2 | 4.0 | ≦0.1 | ≦0.1 |

Microtitre using Nutrient broth
- inoculum 0.001 ml of a $10^{-2}$ dilution for G + ve bacteria or a $10^{-4}$ dilution for G − ve organisms

| ORGANISM | Compound of Example 2 | Compound of Example 4 |
|---|---|---|
| Citrobacter freundii E8 | 12.5 | 25 |
| Enterobacter cloacae N1 | 5.0 | 50 |
| Escherichia coli O111 | 2.5 | 5.0 |
| Escherichia coli JT 39 | 1.2 | 5.0 |
| Klebsiella aerogenes A | 0.5 | 1.2 |
| Proteus mirabilis C977 | 2.5 | 2.5 |
| Proteus morganii I580 | 1.2 | 1.2 |
| Proteus rettgeri WM16 | 5.0 | 12.5 |
| Proteus vulgaris WO91 | 5.0 | 12.5 |
| pseudomonas aeruginosa A | >50 | >50 |
| Salmonella typhimurium CT10 | 1.2 | 50 |
| Serratia marcescens US20 | 5.0 | 12.5 |
| Shigella sonnei MB 11967 | 1.2 | 5.0 |
| Bacillus subtilis A | 0.5 | 0.2 |
| Staphylococcus aureus Oxford | 1.2 | 1.2 |
| Staphylococcus aureus Russell | 1.2 | 1.2 |
| Staphylococcus aureus 1517 | 50 | 25 |
| Streptococcus faecalis I | 25 | 12.5 |
| Streptococcus pneumoniae CN33 | <0.1 | <0.1 |
| Streptococcus pyogenes CN10 | <0.1 | <0.1 |

DST agar + 10% horse blood inoculum 0.001 ml of a $10^{-2}$ dilution for G + ve bacteria or a $10^{-4}$ dilution for G − ve organisms.

We claim:
1. A process for the preparation of a compound of the formula (V):

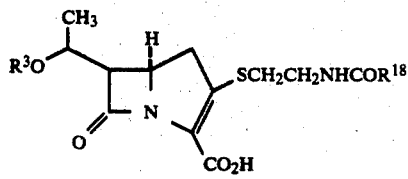

or a pharmaceutically acceptable salt or ester thereof wherein $R^3$ is hydrogen, $HO_3S-$ or $R^5CO$ wherein $R^5$ is alkyl of 1 to 6 carbon atoms, alkenyl of 2 to 6 carbon atoms, aryl, arylalkyl of 1 to 6 carbon atoms in the alkyl moiety or aryloxyalkyl of 1 to 6 carbon atoms in the alkyl moiety wherein the aryl moiety is phenyl unsubstituted or substituted by alkyl of 1 to 3 carbon atoms, alkoxy of 1 to 3 carbon atoms, chloro or fluoro and $R^{18}$ is a group such that the $R^{18}$ —CO—NH moiety is a group of the sub-formulae (a)-(d):

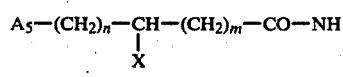  (a)

$A_6-CO-NH$  (b)

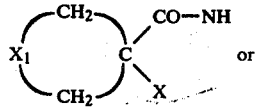  (c)

$A_6-X_2-(CH_2)_n-CO-NH$  (d)

wherein n is 0, 1 or 2; m is 0, 1 or 2; $A_5$ is hydrogen, alkyl of 1-6 carbon atoms, cycloalkyl of 3-6 carbon atoms, cyclohexenyl, cyclohexadienyl, phenyl, hydroxyphenyl, thienyl or pyridyl; X is a hydrogen, fluorine, bromine or chlorine atom, carboxy, a carboxyl ester, azido, tetrazolyl, hydroxy, acyloxy, amino, ureido, guanidino or acylureido group; $A_6$ is phenyl, 2,6-dimethoxyphenyl, 2-alkoxy-1-naphthyl, 3-arylisoxazolyl, isothiazolyl, thiazolyl or 3-aryl-5-methylisoxazolyl wherein aryl is as above defined; $X_1$ is $CH_2OCH_2$, $CH_2SCH_2$ or $(CH_2)n$ wherein n is as above defined; and $X_2$ is an oxygen or sulphur atom, which process comprises the reaction of a pharmaceutically acceptable ester or an ester convertible to a pharmaceutically acceptable ester by chemical or biological methods of a compound of the formula (VI):

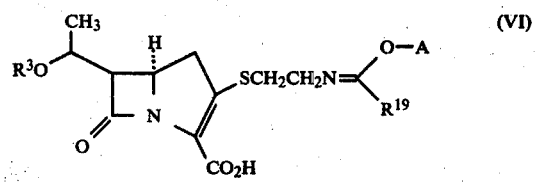

wherein $R^3$ is as above defined except that any group capable of being acylated is optionally protected, A is a hydrocarbon of 1 to 8 carbon atoms, and $R^{19}$ is a group of the sub-formulae (a)-(d) as above defined wherein the moiety —CO—NH is not present and wherein $R^{19}$ is not the same as $R^{18}$; with a catalyst in the presence of an acid acceptor with an N-acylating derivative of a carboxylic acid of the formula (VII):

$$R^{18}CO_2H \tag{VII}$$

wherein $R^{18}$ is a group of the sub-formulae (a)–(d):

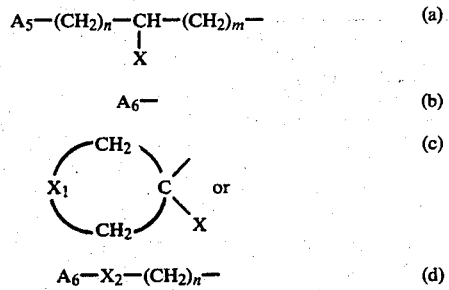

wherein n, m, $A_5$, X, $A_6$, $X_1$ and $X_2$ are as above defined and wherein any group capable of being acylated is optionally protected, and thereafter if necessary:
 (i) converting any cleavable ester group into a free acid, a pharmaceutically acceptable salt or different ester,
 (ii) removing any protecting groups.

2. A process according to claim 1 wherein the catalyst is palladium chloride.

3. A process according to claim 1 which comprises the hydrolysis of an ester of a compound of the formula (VI), and subsequently treating the free amino compound so formed with a reactive acylating derivative of a carboxylic acid of the formula (VII); and thereafter if necessary:
 (i) converting any cleavable ester group into a free acid, a pharmaceutically acceptable salt or different ester, and
 (ii) removing any protecting groups.

4. A process according to claim 1 wherein $R^{19}$ is methyl.

5. A process according to claim 1 wherein A is methyl, ethyl, n-propyl or n-butyl.

6. A process according to claim 1 wherein A is methyl.

7. A process according to claim 1 wherein the acid acceptor is triethylamine, trimethylamine, n-alkylmorpholine, wherein the alkyl moiety is of 1–4 carbon atoms, pyridine or dimethylaminopyridine.

8. A process according to claim 1 wherein the acid acceptor is n-methylmorpholine.

9. A process according to claim 1 wherein the n-acylating agent is an acid chloride or acid bromide.

10. A process according to claim 1 wherein the catalyst is a palladium complex catalyst which is isolated prior to treatment with acylating agent and base.

11. A process accordng to claim 10 wherein the preparation of the intermediate palladium complex is conducted at pH 6 to 8.

12. A process according to claim 11 wherein the process is conducted at a temperature of from 12° to 25° C.